US007867732B2

(12) United States Patent
Hori et al.

(10) Patent No.: US 7,867,732 B2
(45) Date of Patent: Jan. 11, 2011

(54) ISOLATED POLYPEPTIDE BINDING TO A SUGAR CHAIN, POLYNUCLEOTIDE ENCODING THE POLYPEPTIDE AND USE OF THE POLYPEPTIDE AND POLYNUCLEOTIDE

(75) Inventors: Kanji Hori, Higashihiroshima (JP); Haruo Matsuda, Higashihiroshima (JP)

(73) Assignee: National University of Corporation Hiroshima University, Hiroshima (JP)

( * ) Notice: Subject to any disclaimer, the term of this patent is extended or adjusted under 35 U.S.C. 154(b) by 259 days.

(21) Appl. No.: 11/885,282

(22) PCT Filed: Feb. 27, 2006

(86) PCT No.: PCT/JP2006/303604

§ 371 (c)(1),
(2), (4) Date: Jun. 2, 2008

(87) PCT Pub. No.: WO2006/093088

PCT Pub. Date: Sep. 8, 2006

(65) Prior Publication Data

US 2009/0035818 A1    Feb. 5, 2009

(30) Foreign Application Priority Data

Mar. 1, 2005    (JP)    ............... 2005-056717

(51) Int. Cl.
  C12P 21/06    (2006.01)
  C12N 1/20     (2006.01)
  C07K 14/00    (2006.01)
  C07H 21/02    (2006.01)
(52) U.S. Cl. ............... 435/69.1; 435/320.1; 435/252.3; 435/325; 435/410; 530/350; 536/23.1
(58) Field of Classification Search .............. None
See application file for complete search history.

(56) References Cited

U.S. PATENT DOCUMENTS

2002/0164328 A1    11/2002    Shinkawa et al.

FOREIGN PATENT DOCUMENTS

EP            1 333 032 A1    8/2003
WO    WO 2006/093088 A1 *    9/2006

OTHER PUBLICATIONS

Sato et al., Trends Glycosci. Glycotechnol. 16:(Supplement)S52, 2004, 1 page.*
GenBank Accession No. AB278119, Oct. 2009, 2 pages.*
Han et al., Phycological Res. 58:143-150, 2010.*
Extended Search Report issued Dec. 19, 2008 by the European Patent Office in European Patent Application No. 06714741.3.
Kazuo Yamamoto et al. "Requirement of the core structure of a complex-type glycopeptide for the binding to immobilized lentil- and pea-lectins." Carbohydrate Research, 1982, vol. 110, pp. 283-289.
Veerasingham P. Bhavanandan et al. "Isolation and partial characterization of sialoglycopeptides produced by a murine melanoma." Biochemistry, 1977, vol. 16, pp. 4426-4437.
Veerasingham P. Bhavanandan et al. "The interaction of wheat germ agglutinin with sialoglycoproteins: the role of sialic acid." The Journal of Biological Chemistry, 1979, vol. 254, pp. 4000-4008.
Kazuo Yamamoto et al. "Structural requirements for the binding of oligosaccharides and glycopeptides to immobilized wheat germ agglutinin." Biochemistry, 1981, vol. 20, pp. 5894-5899.
Frederick P. Schwarz et al. "Thermodynamics of monosaccharide binding to concanavalin a, pea (*Pisum sativum*) lectin, and lentil (*Lens culinaris*) lectin." The Journal of Biological Chemistry, 1993, vol. 268, pp. 7668-7677.
Rukuro Kaifu et al. "Synthesis of 2-0-(2-acetamido-2-deoxy-β-D-glucopyranosyl)-D-mannose, and its interaction with D-mannose-specific lectins." Carboyhydrate Research, 1975, vol. 40, pp. 111-117.
Hori et al., "A mitogenic agglutinin from the red alaga Carpopeltis Flabellata", Phytochemistry, vol. 26, No. 5, pp. 1335-1338, 1987.
Hori et al., "Hemagglunitins in Marine algae", Bulletin of the Japanese Society of Scientific Fisheries, vol. 47, No. 6, pp. 793-798, 1981.
Hori and Fujiwara, "Novel Seaweed Lectins Having High Binding Selectivity for High-Mannose-Type Sugar Chains", The 1st Annual Meeting of Japanese Society for Marine Biotechnology, Programs and Abstracts, p. 91, 1997.
K.T. Bird et al., "Agglutinins from marien macroalgae of teh southeastern United States", Journal of Applied Phycology, vol. 25, No. 2, pp. 213-218, 1993.
Hori et al., "Isolation and Characterization of Glycoconjugate-specific Isoagglutinins from a Marine Green Alga Boodlea coacta (Dickie) Murray et De Toni", Bontanica Marina, vol. 29, No. 4, pp. 323-328, 1986.

* cited by examiner

*Primary Examiner*—David J Steadman
(74) *Attorney, Agent, or Firm*—Harness, Dickey & Pierce, P.L.C.

(57) ABSTRACT

In one embodiment of the present application, a polypeptide capable of binding to a sugar chain is disclosed, particularly a high-mannose-type sugar chain bound to an antibody, more preferably a sugar chain bound to a chicken antibody. Also disclosed is a method for the purification of an antibody (specifically a chicken antibody) as a representative application of the polypeptide. Further disclosed is means for the purification. The polypeptide, BML-17, is a novel lectin made of 168 amino acid residues isolated from *Bryopsis maxima*. By using BML-17, it becomes possible to purify an antibody (e.g., a chicken antibody) readily and with high efficiency.

9 Claims, 5 Drawing Sheets

FIG. 1
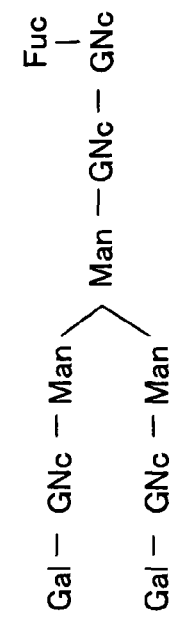
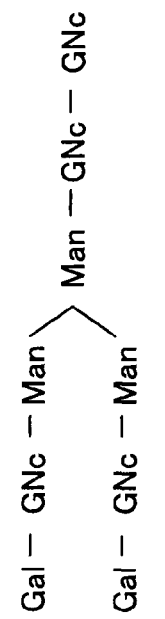
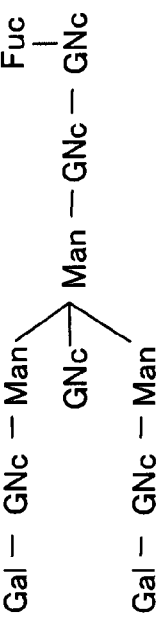
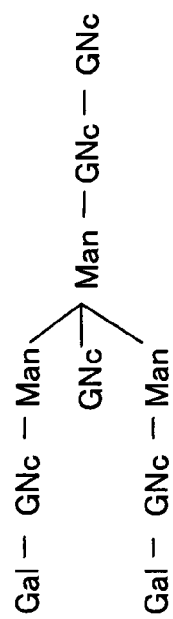
HIGH MANNOSE TYPE SUGAR CHAIN
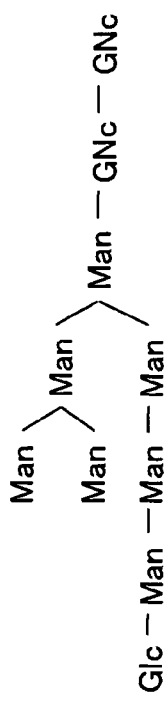
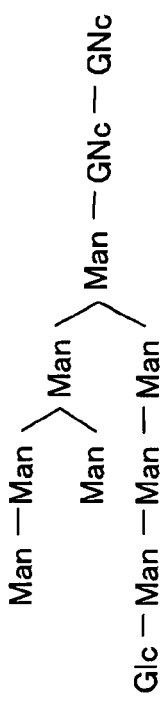
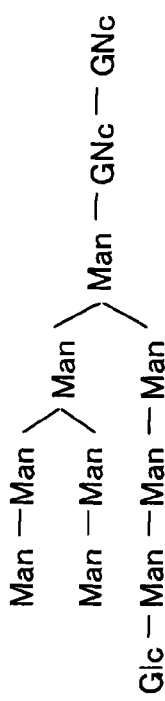
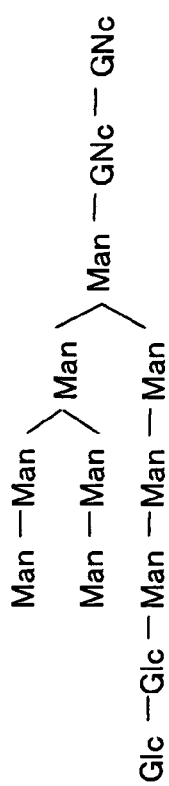
COMPLEX TYPE SUGAR CHAIN

FIG. 2

```
  1  GCCGCACTTGGTGATGCACGGCCAGTTGTCAACCAGATGGCCAACGTCACGACGATGATG   60
  1   A  A  L  G  D  A  R  P  V  V  N  Q  M  A  N  V  T  T  M  M    20
 61  GTTGAAAACGTCATATACCAAGACCCCGTAACTTCAGATATGTTCGCGAAGATTCCGATG  120
 21   V  E  N  V  I  Y  Q  D  P  V  T  S  D  M  F  A  K  I  P  M    40
121  CCGGGGCACCGTGGACCGTGGTACGTCTGCCACTCGTCGGGTGACTGGTCGAGAAACGAG  180
 41   P  G  H  R  G  P  W  Y  V  C  H  S  S  G  D  W  S  R  N  E    60
181  CCTGTTTTCGGCCGTTGTGCCCTGGATGCTAAGGGCATGGTCGAGGCGTACTTCCCCTAT  240
 61   P  V  F  G  R  C  A  L  D  A  K  G  M  V  E  A  Y  F  P  Y    80
241  GGAGGTAAAGACATCAAGTGGCCTTCACGCTGGTCCGCAGTCTTGACCACCGGTGTGTAT  300
 81   G  G  K  D  I  K  W  P  S  R  W  S  A  V  L  T  T  G  V  Y   100
301  TGGGGAAAGTACAACGACTGGAAACAAGCGGATTGCAATGGGGTCAACAAGTGGTGGAC  360
101   W  G  K  Y  N  D  W  K  Q  A  D  C  N  G  G  Q  Q  V  V  D   120
361  GGCGGTAGAGGGGCCGTGACAGTCAGGATGGACGGACTCTCGGAGTGCAAGGGCTGGACA  420
121   G  G  R  G  A  V  T  V  R  M  D  G  L  S  E  C  K  G  W  T   140
421  ACGGGTAAGAGAGCAGTCATAACGAGAGTTCTGGTTCGGATGTAACGAAAGGAGGTGGGTAGC  480
141   T  G  K  S  S  H  N  E  V  W  F  G  C  N  G  K  E  V  G  S   160
481  TGGCTGTCTGATACCCCTGCCAGCGACGTTTTCCCTCTGTGCCAGGAGTATGGAGCGGCA  540
161   W  L  S  D  T  P  A  S  D  V  F  P  L  C  Q  E  Y  G  A  A   180
541  GTAAAATTGGTCCACATGGGGCGCCTTTCAACTAA                            576
181   V  K  L  V  H  M  G  R  A  F  N  *                            191
```

☐ SIGNAL PEPTIDE REGION   *, END CODON

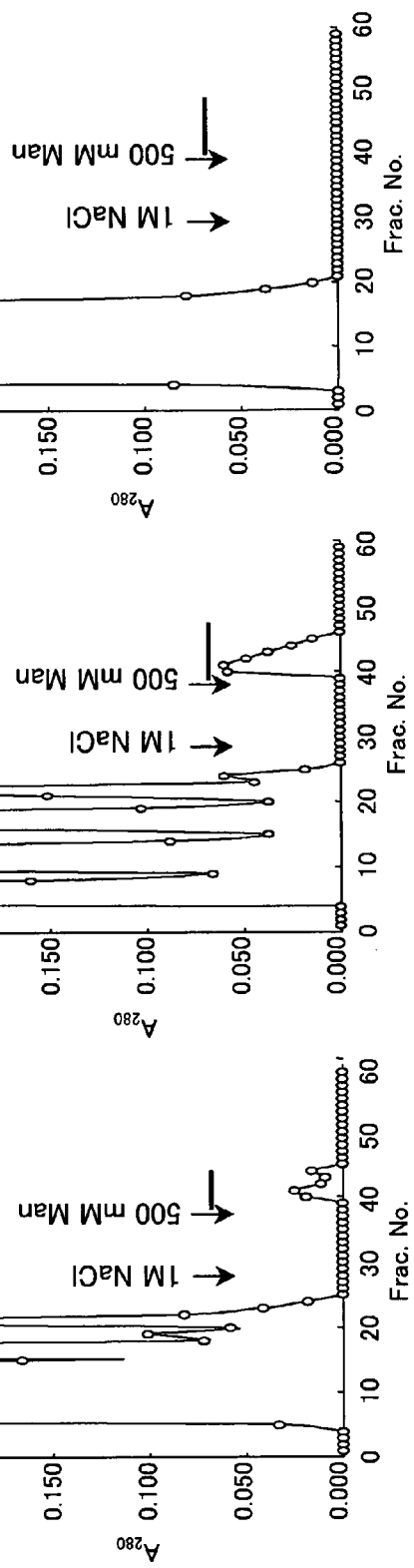

ISOLATED POLYPEPTIDE BINDING TO A SUGAR CHAIN, POLYNUCLEOTIDE ENCODING THE POLYPEPTIDE AND USE OF THE POLYPEPTIDE AND POLYNUCLEOTIDE

TECHNICAL FIELD

The present invention relates to novel polypeptides that bind to sugar chains, particularly high-mannose-type sugar chains. The invention also relates to polynucleotides that encode the polypeptides, and representative uses of the polypeptides and polynucleotides.

BACKGROUND ART

As the proteins (polypeptides) that bind to sugar chains, there have been known sugar-binding proteins, lectins, and lectin-like substances, such as mannose-binding proteins, fibroblast growth factors, and epidermal growth factors. The property of lectin is such that it specifically binds to specific sugar structure. This allows the lectins to be purified using a column on which sugars, sugar chains, or complex carbohydrates are immobilized. Wheat germ lectin and lentil lectin are some of the examples of lectins.

The binding activity of the wheat germ lectin and sugar chain or glycopeptide has been investigated, which suggested that the wheat germ lectin has strong affinity for hybrid type sugar chains among N-glycosidic-binding sugar chains, or sugar chains or glycopeptides having sialic acid (see Non-Patent Publications 1 and 2). It is also known that the wheat germ lectin has stronger binding activity for glycopeptides having a sugar chain structure containing bisecting N-acetylglucosamine (see Non-Patent Publication 3).

It is known that the lentil lectin recognizes the monosaccharides, α-D-mannose and α-D-glucose (see Non-Patent Publication 4). It is also known that the lentil lectin has strong affinity for glycopeptides having a sugar chain in which L-fucose is attached to the α1,6 position of the N-acetylglucosamine residue closest in position to the asparagine of the N-glycosidic-binding sugar chain (see Non-Patent Publications 5 and 6).

Meanwhile, the antibody is known to include a sugar chain structure specific to its Fc region. Purification of antibody is then possible by taking advantage of binding of lectins with the sugar chain. As a method of purifying antibody (particularly, human antibody) using lectins, the method described in Patent Publication 1 is known, for example.

Phylogenetically, chicken is classified lower than mammals; however, they have a sophisticated immune system similar to that of mammals. Specifically, due to the phylogenetic distance from mammals, chicken is useful for the production of specific antibodies against proteins conserved in many mammals. That is, chicken can be used to produce specific antibodies against proteins (antigens), which is difficult to achieve with mice and rats. For example, the antibody against N-acetylneuraminic acid, the antigen as a cancer marker in humans, cannot be produced in animals such as mice or rats because N-glycolylneuraminic acid is present in almost all mammals except humans. Production of the antibody is possible in birds such as chicken, because N-acetylneuraminic acid is not present in birds. Further, production of antibody against the pathogenic prion protein that causes Creutzfeldt-Jakob disease or mad cow disease is also difficult in mammals due to the 90% or greater homology among mammals. The homology between mammal and bird is on the order of 30%, which allows for production of antibody against this particular antigen. In fact, the inventors of the present invention have succeeded in producing chicken monoclonal antibodies against N-acetylneuraminic acid and prion protein by the cell fusion method. Among other advantages of the chicken antibody, use of chicken monoclonal antibody and mammal monoclonal antibody makes it possible to establish a highly sensitive antigen detecting system in which no non-specific reaction occurs, because there is no cross reactivity with the mammal antibody.

As described above, usefulness of chicken antibody (antibody produced by chicken, antibody having the same structure as the antibody produced by chicken), for example, in test and medical applications has been looked into, and establishment of methods for efficiently producing and purifying the chicken antibody is called for. As to the producing method of chicken antibody, progress has been made by techniques such as the cell fusion method and phage display method. However, a further development is needed for the establishment of the purification method.

The chicken antibody does not bind to proteins A and G used as ligands for purifying IgG antibody of mammals. Thus, the method intended for mammals cannot be used directly.

In order to develop a purification technique for chicken antibody, the inventors of the present invention attempted to purify chicken antibody using an affinity column with mouse monoclonal antibody. However, this method failed to purify the chicken antibody. The inventors of the present invention then attempted to purify chicken antibody using gel filtration and ion exchange column. As a result, electrophoretically uniform antibody was successfully purified. However, this method had drawbacks in that it required many steps, was complex, and had a considerably low yield. Among other problems, the purified antibody had a low titer.

In order to overcome such drawbacks, the inventors of the present invention attempted to purify chicken antibody using plant-derived lectins (saxifrage-derived lectin, lentil-derived lectin, and Con A) that specifically bind to the high-mannose-type sugar chains, by taking advantage of the fact that the chicken antibody contains the high-mannose-type sugar chains. However, while the antibody was adsorbed on the saxifrage-derived lectin and the lentil-derived lectin, the antibody could not be eluted. In the case of Con A, the antibody was adsorbed and was eluted with α-methyl glucoside. However, electrophoretically uniform antibody could not be obtained. This was considered to be due to the specific structure of the sugar chain binding to the chicken antibody.

Currently, almost nothing has been revealed as to the sugar chain structure of the chicken antibody (chicken monoclonal antibody). There has been a recent report that the N-asparagine-binding sugar chain (hereinafter, "N-type sugar chain") of chicken egg yolk antibody (hereinafter, "IgY antibody") contains glucose on the order of 10% (Ohta, M. et al., Glycoconj. J., 8, 400-413 (1991)). The fact that the N-type sugar chain of mammal IgG antibody does not contain any glucose suggests that the chicken antibody has a unique sugar chain structure. It may therefore be difficult to purify the chicken antibody by directly using the lectins that enable purification of mammal antibodies. It was inferred from the analysis of sugar chain by the inventors of the present invention that the chicken antibody contained both the high-mannose-type sugar chain and the complex type sugar chain, and that more than one glucose was present at the non-reducing end of the sugar chains, or more specifically, one glucose at the non-reducing end of the sugar chain of chicken IgY antibody.

The present invention was made in view of the foregoing problems, and it is an object of the present invention to find a polypeptide (for example, lectin) that binds to a sugar chain, or more specifically a high-mannose-type sugar chain attached to antibody, or more specifically a sugar chain binding to the chicken antibody. The invention also provides a method and means for purifying antibody (particularly, chicken antibody), as representative uses of the polypeptide. It is a further object of the invention to provide a polynucleotide that encodes the polypeptide, an antibody that binds to the polypeptide, and uses of such polynucleotides and antibodies.

[Patent Publication 1]
International Publication WO 02/30954, Pamphlet (published on Apr. 18, 2002)
[Non-Patent Publication 1]
Biochemistry, 16, 4426, 1977
[Non-Patent Publication 2]
The Journal of Biological Chemistry, 254, 4000, 1979
[Non-Patent Publication 3]
Biochemistry, 20, 5894, 1981
[Non-Patent Publication 4]
The Journal of Biological Chemistry, 268, 7668, 1993
[Non-Patent Publication 5]
Carbohydrate Research, 40, 111, 1975
[Non-Patent Publication 6]
Carbohydrate Research, 110, 283, 1975

DISCLOSURE OF INVENTION

In order to achieve the foregoing objects, the inventors of the present invention looked into lectins, and particularly algae-(seaweed)-derived lectins, and searched for lectins that were capable binding to a high-mannose-type sugar chain, specific to chicken antibody, having glucose at the non-reducing end. A polypeptide according to the present invention was found as a result.

In order to achieve the foregoing objects, the present invention provides a polypeptide which binds to a sugar chain, the polypeptide consisting of: (a) an amino acid sequence of SEQ ID NO: 2; or (b) an amino acid sequence with a substitution, deletion, insertion, or addition of one or several amino acids in the amino acid sequence of SEQ ID NO: 2.

In order to achieve the foregoing objects, a polypeptide according to the present invention may be adapted such that the sugar chain is a high-mannose-type sugar chain.

In order to achieve the foregoing objects, a polypeptide according to the present invention may be adapted such that the sugar chain includes at least one glucose attached to the non-reducing end.

In order to achieve the foregoing objects, the present invention provides an antibody which binds to a polypeptide of the present invention.

In order to achieve the foregoing objects, the present invention provides a polynucleotide that encodes a polypeptide according to the present invention.

In order to achieve the foregoing object, a polynucleotide according to the present invention may be adapted such that it is selected from: (a) a polynucleotide consisting of a base sequence of SEQ ID NO: 1; or (b) a polynucleotide that hybridizes under stringent conditions with (i) the polynucleotide consisting of the base sequence of SEQ ID NO: 1, or (ii) a polynucleotide consisting of a base sequence complementary to the base sequence of SEQ ID NO: 1.

In order to achieve the foregoing object, the present invention provides a vector which comprises a polynucleotide according to the present invention.

In order to achieve the foregoing object, the present invention provides a method for producing a polypeptide according to the present invention, using a vector according to the present invention.

In order to achieve the foregoing object, the present invention provides a transformant in which a polynucleotide according to the present invention is introduced.

In order to achieve the foregoing object, a method for producing a polypeptide according to the present invention may be adapted to use a transformant according to the present invention.

In order to achieve the foregoing object, the present invention provides a detecting instrument which includes a substrate on which a polynucleotide according to the present invention is immobilized.

In order to achieve the foregoing object, a detecting instrument according to the present invention may be adapted to include a substrate on which a polypeptide according to the present invention is immobilized.

In order to achieve the foregoing object, a detecting instrument according to the present invention may be adapted to include a substrate on which an antibody according to the present invention is immobilized.

In order to achieve the foregoing object, the present invention provides a method for purifying a polypeptide according to the present invention, in which an antibody according to the present invention is used.

In order to achieve the foregoing object, the present invention provides a method for purifying an antibody, in which a polypeptide according to the present invention is used. In order to achieve the foregoing object, a method for purifying an antibody according to the present invention may be adapted to use Carnin, in addition to a polypeptide according to the present invention. In order to achieve the foregoing object, a method for purifying an antibody according to the present invention may be adapted to use one of or both of a polypeptide according to the present invention and Carnin.

In order to achieve the foregoing object, a method for purifying an antibody according to the present invention uses a chicken antibody as the antibody.

In order to achieve the foregoing object, the present invention provides a support on which a polypeptide according to the present invention is immobilized. In order to achieve the foregoing object, a support according to the present invention may be adapted to immobilize Carnin, in addition to a polypeptide according to the present invention. In order to achieve the foregoing object, a support according to the present invention may be adapted to use one of or both of a polypeptide according to the present invent on and Carnin.

A polypeptide according to the present invention is capable of binding to a sugar chain, and particularly a high-mannose-type sugar chain. This allows for purification of various antibodies using the polypeptide. Further, a polypeptide according to the present invention is capable of binding to a sugar chain specific to chicken antibody, i.e., a high-mannose-type sugar chain including at least one glucose at the non-reducing end. A polypeptide according to the present invention is therefore particularly suitable for the purification of chicken antibody, and allows for efficient purification. Note that, the known lectin, Carnin, can also be used in the same manner.

A polynucleotide according to the present invention encodes a polypeptide according to the present invention. Thus, a polypeptide according to the present invention can be produced both easily and in mass quantity, by using a polynucleotide according to the present invention, a vector including the polynucleotide, and a transformant to which the polynucleotide has been introduced.

An antibody according to the present invention is capable of binding to a polypeptide according to the present invention. Thus, a polypeptide according to the present invention can be efficiently purified from a crude solution of the polypeptide by immobilizing the antibody on a support and performing affinity chromatography, for example.

Additional objects, features, and strengths of the present invention will be made clear by the description below. Further, the advantages of the present invention will be evident from the following explanation.

BRIEF DESCRIPTION OF DRAWINGS

FIG. 1 is a diagram showing sugar chain structures of chicken antibodies.

FIG. 2 is a diagram showing a base sequence of full-length cDNA of BML-17, and an amino acid sequence determined from the base sequence.

FIG. 5(a) is a diagram representing a result of monitoring protein behaviors at UV 280 nm absorption ($A_{280}$), when hybridoma culture supernatant was passed through the column (BML-17 column) immobilizing the lectin, and when elution was performed with 500 mM D-mannose, in an experiment performed in Example 7.

FIG. 5(b) is a diagram representing a result of monitoring protein behaviors at UV 280 nm absorption ($A_{280}$), when hybridoma culture supernatant was passed through the column (Carnin column) immobilizing the lectin, and when elution was performed with 500 mM D-mannose, in an experiment performed in Example 7.

FIG. 5(c) is a diagram representing a result of monitoring protein behaviors at UV 280 nm absorption ($A_{280}$), when hybridoma culture supernatant was passed through the column (Con A column) immobilizing the lectin, and when elution was performed with 500 mM D-mannose, in an experiment performed in Example 7.

FIG. 5(d) is a diagram representing a result of monitoring protein behaviors at UV 280 nm absorption ($A_{280}$), when hybridoma culture supernatant was passed through the column (Con A-HiTrap column) immobilizing the lectin, and when elution was performed with 500 mM D-mannose, in an experiment performed in Example 7.

FIG. 5(e) is a diagram representing a result of monitoring protein behaviors at UV 280 nm absorption ($A_{280}$), when hybridoma culture supernatant was passed through the IgY purifying column (commercial product), and when elution was performed with elution buffer (commercial product), in an experiment performed in Example 7.

FIG. 6(a) is a diagram according to Example 7 representing a result of western blotting performed on eluants obtained when hybridoma culture supernatant was passed through the columns on which various lectins were immobilized (BML-17 column, Carnin column, Con A column, Con A-HiTrap column), and the IgY purifying column, and when elution was performed with 500 mM D-mannose or elution buffer.

FIG. 6(b) is a diagram according to Example 7 representing a result of SDS-PAGE performed on eluants obtained when hybridoma culture supernatant was passed through the columns on which various lectins were immobilized (BML-17 column, Carnin column, Con A column, Con A-HiTrap column), and the IgY purifying column, and when elution was performed with 500 mM D-mannose or elution buffer.

FIG. 7 is a diagram according to Example 1 showing a result of SDS-PAGE (10% gel) performed on purified fractions from algae (*Bryopsis maxima*).

FIG. 8 is a diagram representing an N-terminal amino acid sequence of BML-17, and an N-terminal amino acid sequence of previously isolated *Bryopsis* lectins (BCL, BPL, Bry-1, Bry-2).

FIG. 9 is a sensorgram representing interactions between immobilized tyroglobulin and various lectins.

BEST MODE FOR CARRYING OUT THE INVENTION

Figure 3:
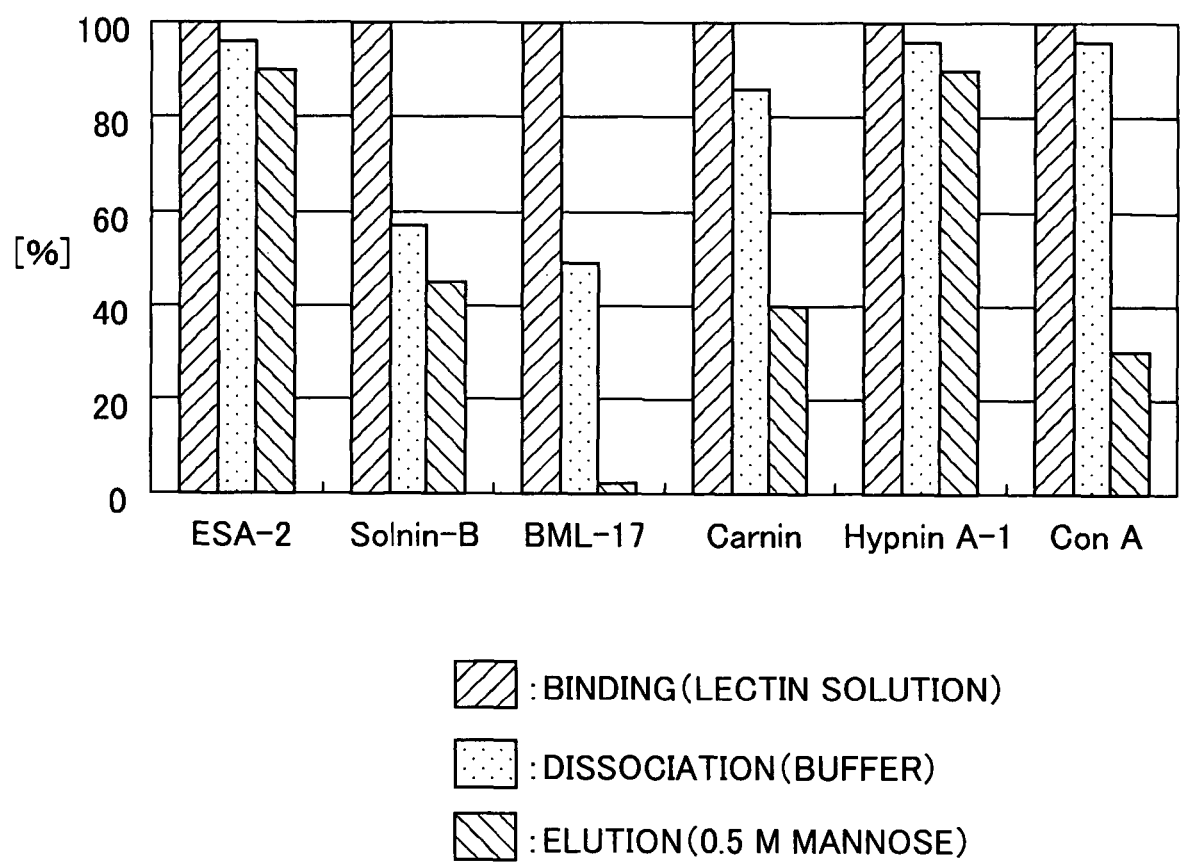
FIG. 3 is a histogram according to Example 5 representing results of experiment on binding, dissociation, and elution of various kinds of lectins (ESA-2, Solnin B, BML-17, Carnin, Hypnin A-1, Con A) using a bovine tyroglobulin-immobilized chip.

The following will describe one embodiment of the present invention. It should be noted that the present invention is not limited by the following description.

First, description is made as to a polypeptide according to the present invention, a polynucleotide encoding the polypeptide, and use of the polypeptide and polynucleotide.

(1) Polypeptide

The inventors of the present invention accomplished the invention based on the findings that a polypeptide (hereinafter, referred to as "BML-17") isolated from seaweed (*Bryopsis maxima*) was capable of binding to sugar chains, particularly high-mannose-type sugar chains, and sugar chains specific to chicken antibodies (i.e., high-mannose-type sugar chains having at least one glucose attached to the non-reducing end), and that the BML-17 was suitable for the purification of chicken antibodies (IgY antibody, etc.). Such effects were also confirmed in Carnin, which is a lectin derived from the known alga (*Carpopeltis flabellata=C. prorifera*).

As used herein, the term "polypeptide" is used interchangeably with "peptide" or "protein." A polypeptide according to the present invention may be isolated from natural sources, or chemically synthesized.

The term "isolated" is intended polypeptides or proteins removed from the natural environment in which they reside. For example, recombinant polypeptides and proteins expressed in host cells can be regarded as being "isolated" as are natural or recombinant polypeptides and proteins that have been substantially purified by any appropriate techniques.

A polypeptide according to the present invention includes purified products from nature, products of chemical synthesis procedures, and products of recombinant techniques using prokaryotic or eukaryotic hosts (for example, bacterial cells, yeast cells, higher plant cells, insect cells, and mammalian cells). A polypeptide according to the present invention may be glycosylated or non-glycosylated, depending upon the host used in the recombination procedures. Further, in some cases, a polypeptide according to the present invention may include a start modified methionine residue as a result of a host-mediated process.

The present invention provides a polypeptide according to the present invention. In one embodiment, a polypeptide according to the present invention is a polypeptide consisting of the amino acid sequence of SEQ ID NO: 2, or a mutant of a polypeptide consisting of the amino acid sequence of SEQ ID NO: 2.

Such mutants include deletions, insertions, inversions, repeats, and type substitutions (for example, substituting one hydrophilic residue for another, but not strongly hydrophobic for strongly hydrophilic as a rule). Such "neutral" amino acid substitutions will generally have little effect on activity of the polypeptide.

It will be recognized in the art that some amino acids in the amino acid sequence of the polypeptide can be varied without significant effect on the structure or function of the polypeptide. It is also known that such a mutant with no significant structural or functional change occurs not only in artificially modified proteins but in nature as well.

It is easy for a person ordinary skill in the art to modify one or several amino acids in the amino acid sequence of a polypeptide using a conventional technique. For example, by a conventional point mutation introducing method, any base of a polynucleotide that encodes a polypeptide can be mutated. Further, with primers that are designed to correspond to arbitrary sites of a polynucleotide that encodes a polypeptide, a deletion mutant or an addition mutant can be produced. Further, with the method described in the present invention, whether or not the mutant is according to the present invention can easily be evaluated.

The mutants preferably include those produced by substitutions, deletions, or additions of amino acid, which may be conservative or non-conservative. Especially preferred among these are silent substitutions, additions and deletions. Also especially preferred are conservative substitutions. These do not alter the polypeptide activity according to the present invention.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," Science 247:1306-1310 (1990) (herein incorporated by reference).

A polypeptide according to the present embodiment is preferably a polypeptide that binds to a sugar chain and that consists of:

(a) the amino acid sequence of SEQ ID NO: 2; or (b) the amino acid sequence of SEQ ID NO: 2 with a substitution, deletion, insertion, or addition of one or several amino acids.

As used herein, the "substitution, deletion, insertion, or addition of one or more amino acids" means substitution, deletion, insertion, or addition of numbers of amino acids (for example, preferably no greater than 10, more preferably no greater than 7, most preferably no greater than 5) that can be brought about by known mutant polypeptide producing methods such as site-directed mutagenesis. Such a mutant polypeptide is not just limited to polypeptides that are artificially mutated by known mutant polypeptide producing methods, but may be isolated and purified from polypeptides that exist in nature.

A polypeptide according to the present invention is formed of amino acids joined together by peptide bonding. However, a polypeptide according to the present invention is not just limited to this example and may be a complex polypeptide including a non-polypeptide structure. As used herein, the "non-polypeptide structure" includes, but is not particularly limited to, sugar chains and isoprenoid groups, for example.

A polypeptide according to the present invention may include additional polypeptides. For example, the polypeptide may be epitope-labeled with His, Myc, or Flag.

Further, a polypeptide according to the present invention may be expressed intracellularly by being encoded by a polynucleotide according to the present invention (polynucleotide encoding a polypeptide according to the present invention; to be described later) that has been introduced into a host cell. Alternatively, a polypeptide according to the present invention may be isolated and purified from cells or tissues. Further, a polypeptide according to the present invention may be chemically synthesized.

In another embodiment, a polypeptide according to the present invention may be recombinantly expressed in a modified form, such as a fusion protein. For instance, a region of additional amino acids of polypeptide according to the present invention, particularly charged amino acids, may be added to the N-terminal of the polypeptide to improve stability and persistence in the host cell, during purification, or during subsequent handling and storage.

A polypeptide according to the present embodiment may be fused at the N- or C-terminal to a tag label (tag sequence or marker sequence), such as a sequence encoding a peptide which facilitates purification of the fused polypeptide. Such sequences may be removed prior to final preparation of the polypeptide. In certain preferred embodiments of this aspect of the invention, the tagged amino acid sequence is a hexa-histidine peptide, such as the tag provided in a pQE vector (Qiagen, Inc.), among others, many of which are publicly/commercially available. As described in Gentz et al., Proc. Natl. Acad. Sci. USA 86:821-824 (1989) (incorporated herein by reference), for instance, hexa-histidine provides for convenient purification of the fusion protein. The "HA" tag is another peptide useful for purification which corresponds to an epitope derived from the influenza hemagglutinin (HA) protein, which has been described by Wilson et al., Cell 37: 767 (1984) (incorporated herein by reference). As discussed below, other such fusion proteins include a polypeptide according to the present embodiment, or a fragment thereof, fused to Fc at the N- or C-terminal.

In another embodiment, a polypeptide according to the present invention may be obtained by recombination, or chemically synthesized, as described below.

Recombination may be performed by methods known in the art, using vectors and cells described below, for example.

The synthetic peptide may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized in less than four weeks (Houghten, R. A. Proc. Natl. Acad. Sci. USA 82:5131-5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously (Houghten, et al., supra, p. 5134). These publications are hereby incorporated by reference.

As will be described later, a polypeptide according to the present invention is useful for methods and kits for purifying antibody (chicken antibody, in particular).

The inventors of the present invention found that a polypeptide according to the present invention binds to sugar chains, and, particularly, high-mannose-type sugar chains, and further, high-mannose-type sugar chains to which at least one glucose is attached at the non-reducing end. As used herein, the "sugar chains" means oligosaccharides or polysaccharides with straight or branched chains. Depending upon the manner in which the bond is formed with protein, the sugar chains are broadly divided into N-glycosidic-binding sugar chains, which bind to asparagine (hereinafter, "N-type sugar chains"), and O-glycosidic-binding sugar chains, which bind to serine, threonine, or the like (hereinafter, "O-type sugar chains"). The N-type sugar chains include high-mannose-type sugar chains, complex type sugar chains, and hybrid type sugar chains. In the present invention, all of these sugar chains are included.

Oligosaccharides refer to carbohydrates with 2 to 10 monosaccharides or substituted derivatives of monosaccharides linked together by dehydration. Carbohydrates with greater numbers of monosaccharides are referred to as polysaccharides. The polysaccharide is called acidic polysaccharide if it contains a large number of uronic acids or sulfate ester, and neutral polysaccharide if it contains only neutral sugars, though it depends on the type of sugar it contains. Among polysaccharides, almost all of polysaccharides in a group of polysaccharides called mucopolysaccharides bind to proteins, and are known as proteoglycans. The monosaccharide is the constituting unit of sugar chains, i.e., fundamental substance that cannot be broken down into a simpler molecule by hydrolysis.

The monosaccharide is broadly divided into three classes of sugars: acidic sugars having acidic side chains such as carboxyl groups; amino sugars in which a hydroxy group is substituted with an amino group; and neutral sugars which do not classify as either of the acidic sugars and the amino sugars. These monosaccharides are found in living organisms. For example, the acidic sugar exists as sialic acid, such as N-acetylneuraminic acid or N-glycolylneuraminic acid (hereinafter, "Neu5Gc"), or uronic acid. The amino sugar exists as, for example, N-acetylglucosamine (hereinafter, "GlcNAc") or N-acetylgalactosamine. The neutral sugar exists as, for example, glucose, mannose, galactose, or fucose.

The sugar chains that bind to the antibody include all of the three types of N-type sugar chains. The N-type sugar chains all include a common core structure made up of [Manα1-6(Manα1-3)Manβ1-4GlcNAcβ1-4GlcNAc] known as the "trimannosyl core." The high-mannose-type sugar chain includes only the α-mannose residue at the branch structure portion, in addition to the trimannosyl core. This type of sugar chain includes a common core structure with 7 sugars [Manα1-6(Manα1-3)Manα1-6(Manα1-3) Manβ1-4GlcNAcβ1-4GlcNAc]. The name "hybrid type" sugar chain originates from the characteristics of the sugar chain including the both characteristics of the complex type sugar chain and the high-mannose-type sugar chain. As in the high-mannose-type, one or two α-mannosyl groups are bound to the Manα1-6 arm of the trimannosyl core, and the same sugar chain found in the side chain of the complex type sugar chain is bound to the Manα1-3 arm of the core. The diversity of the complex type and hybrid type sugar chain structures is attributed to the presence and absence of the fucose bond to the C-6 position of GlcNAc at the reducing end of the trimannosyl core, and the presence and absence of the GlcNAc residue attached to β-mannosyl residue at the C-4 position (known as bisecting GlcNAc). Among the three kinds of N-type sugar chains, the structure of the complex type is most diverse. Two main factors contribute to such diversity. One to five side chains are bound to the trimannosyl core at different positions to form 1, 2, 3, 4, or 5 side sugar chains. In the complex type sugar chain with 3 side chains, two isomers have been found, which include either [GlcNAcβ1-4(GlcNAcβ1-2)Manα1-3] or [GlcNAcβ1-6 (GlcNAcβ1-2)Manα1-6].

In the trimannosyl core, the end of sugar chain bound to asparagine, i.e., the end on the GlcNAc side, is called a reducing end. The opposite end, i.e., the end on the Man side, is called a non-reducing end. Analysis of sugar chain conducted by the inventors of the present invention has revealed that the high-mannose-type sugar chain and complex type sugar chain is bound to chicken antibody (chicken IgY antibody, etc.), and that at least one glucose is present at the non-reducing end of the high-mannose-type sugar chain. More specifically, it is known that one glucose is present at the non-reducing end of the high-mannose-type sugar chain of chicken IgY antibody. FIG. 1 represents sugar chain structures of chicken antibody. Shown on the left of FIG. 1 are structures of high-mannose-type sugar chains bound to chicken antibody. Structures of complex type sugar chains are shown on the right-hand-side of FIG. 1. As described above, chicken antibody includes one or two glucoses at the non-reducing end. One glucose is present at the non-reducing end of the sugar chain of chicken IgY antibody. Note that, binding of the complex type sugar chain is common to all classes of immunoglobulins.

Whether the polypeptide binds to the sugar chain can be evaluated according to the following procedure. For example, a test polypeptide is flown through a column on which a sugar chain, an antibody bearing the sugar chain, or glycoprotein, etc. is immobilized, and whether the polypeptide binds to the column is determined from the amount of polypeptide contained in the solution discharged from the column, or from the amount of polypeptide eluted from the column with a specific eluent. Alternatively, evaluation may be made by a western blot method (*Hou Igaku No Jissai To Kenkyu,* 37, 155, 1994) or a dot blot method (Analytical Biochemistry, 204(1), 198, 1992), in which antibodies bearing target sugar chains are immobilized on a membrane or the like, and are detected with polypeptides that have been labeled with biotin, fluorescein isothiocyanate, peroxidase, or the like. Further, surface plasmon resonance method (SPR method) may be used for the measurement of affinity of the test polypeptide with a chip on which a target sugar chain, an antibody bearing the sugar chain, or glycoprotein, etc. is immobilized. This technique is preferable because it can detect not only the presence or absence of affinity but also the strength of affinity as well. The polypeptide and the sugar chain can be said to have bonded when the resulting affinity constant ($K_A$) is equal to or greater than 10 (M$^{-1}$), more preferably equal to or greater than 10$^3$ (M$^{-1}$), or most preferably equal to or greater than 10$^4$ (M$^{-1}$).

A polypeptide according to the present invention may include at least the amino acid sequence of SEQ ID NO: 2. It should therefore be appreciated that a polypeptide including the amino acid sequence of SEQ ID NO: 2, and any other amino acid sequence with a specific functionality (for example, tag) is also included in the present invention. The amino acid sequence of SEQ ID NO: 2 and such additional amino acid sequence may be joined together with a suitable linker peptide, provided that it does not inhibit the functions of the amino acid sequences.

That is, an object of the present invention is to provide a polypeptide according to the present invention. As such, the invention is not just limited to, for example, the specific methods of producing polypeptides. It should therefore be appreciated that a polypeptide according to the present invention obtained by other methods also falls within the scope of the present invention.

(2) Polynucleotide

The present invention provides a polynucleotide that binds to a sugar chain (hereinafter referred to as "polynucleotide according to the present invention"). As used herein, the term "polynucleotide" is used interchangeably with "nucleic acid" or "nucleic acid molecule," and a collection of nucleotides is intended. As used herein, "base sequence" is used interchangeably with "nucleic acid sequence" or "nucleotide sequence," and it is represented by a sequence of deoxyribonucleotides (A, G, C, and T).

A polynucleotide according to the present invention may be in the form of RNA (for example, mRNA) or DNA (for example, cDNA or genomic DNA). The DNA may be double stranded or single stranded. The single strand DNA or RNA may be a coding strand (also known as a sense strand) or a non-coding strand (also known as an anti-sense strand).

As used herein, the term "oligonucleotide" refers to a molecule of several to several ten nucleotides, and it is used interchangeably with "polynucleotide." The oligonucleotide is denoted by the number of nucleotides it contains. For example, the term dinucleotide (dimer) or trinucleotide (trimer) is used to refer to oligonucleotides of short sequences, whereas long oligonucleotides are referred to as 30 mers or 100 mers. The oligonucleotide may be produced as a fragment of a polynucleotide, or alternatively chemically synthesized.

A fragment of a polynucleotide according to the present invention is intended a fragment of at least 12 nt (nucleotides), preferably about 15 nt, more preferably at least about 20 nt, further preferably at least about 30 nt, or even more preferably at least about 40 nt in length. By "a fragment at least 20 nt in length" is intended fragments which include 20 or more contiguous bases in the base sequence of SEQ ID NO: 1, for example. Since the base sequence of SEQ ID NO: 1 is provided by an embodiment of the present invention, generating such DNA fragments based on SEQ ID NO: 1 would be routine to the skilled artisan. For example, restriction endonuclease cleavage or shearing by sonication could easily be used to generate fragments of various sizes. Alternatively, such fragments could be generated synthetically. Suitable fragments (oligonucleotides) are synthesized with the Synthesizer Type 392 of Applied Biosystems Incorporated (ABI, 850 Lincoln Center Dr., Foster City, Calif. 94404).

A polynucleotide according to the present invention may be fused with a polynucleotide encoding the tag label (tag sequence or marker sequence) at 5' or 3' region.

The present invention also relates to mutants of a polynucleotide encoding a polypeptide according to the present invention. "Mutants" can occur naturally, such as a natural allelic variant. By an "allelic variant" is intended one of several alternate forms of a gene occupying a given locus on a chromosome of an organism. Non-naturally occurring variants can be produced, e.g., using art-known mutagenesis techniques.

For example, the mutant may include deletion, substitution, or addition of one or several bases in the base sequence of a polynucleotide encoding a polypeptide according to the present invention. The mutant may have a mutation in the coding region or non-coding region, or both of these regions. The mutation in the coding region may be deletion, substitution, or addition of amino acid, which may be conservative or non-conservative.

The present invention also provides an isolated polynucleotide, which includes a polynucleotide encoding a polypeptide according to the present invention, or a polynucleotide that hybridizes with the polynucleotide under stringent hybridization conditions.

In one embodiment, a polynucleotide according to the present invention is preferably a polynucleotide that encodes a polypeptide according to the present invention, and that encodes:

(a) a polypeptide consisting of the amino acid sequence of SEQ ID NO: 2; or (b) a polypeptide with the substitution, deletion, insertion, or addition of one or several amino acids in the amino acid sequence of SEQ ID NO: 2.

In another embodiment, a polynucleotide according to the present invention is preferably a polynucleotide that encodes a polypeptide according to the present invention, and that is selected from:

(a) a polynucleotide consisting of the base sequence of SEQ ID NO: 1; or (b) a polynucleotide that hybridizes under stringent conditions with (i) a polynucleotide consisting of the base sequence of SEQ ID NO: 1, or (ii) a polynucleotide consisting of a base sequence complementary to the base sequence of SEQ ID NO: 1.

As used herein, "under stringent conditions" means that hybridization occurs only when the sequences share at least 90% identity, preferably at least 95% identity, or most preferably at least 97% identity.

Hybridization can be performed by conventional methods, for example, according to the procedure described in J. Sambrook et al. Molecular Cloning, A Laboratory Manual, 2nd Ed., Cold Spring Harbor Laboratory (1989). As a rule, the level of stringency increases (more difficult to hybridize) with increase in temperature and decrease in salt concentration, making it possible to obtain more homologous polynucleotides. Hybridization can suitably be performed under conventional conditions. Though not limited to the following, hybridization can be performed under the following conditions, for example: 42° C., 6×SSPE, 50% formamide, 1% SDS, 100 µg/ml salmon sperm DNA, 5× Denhart solution (1×SSPE; 0.18 M sodium chloride, 10 mM sodium phosphate, pH 7.7, 1 mM EDTA. 5×Denhart solution; 0.1% bovine serum albumin, 0.1% Ficoll, 0.1% polyvinyl pyrrolidone).

A polynucleotide or oligonucleotide according to the present invention includes not only double-stranded DNA but also single-stranded DNA or RNA, or a sense strand or antisense strand, constituting the double strand. The DNA includes cDNA or genomic DNA that can be obtained by cloning, chemical synthesis techniques, or a combination of these different techniques, for example. A polynucleotide or oligonucleotide according to the present invention may include sequences such as a sequence of untranslated region (UTR), or a vector sequence (including expression vector sequence).

A polynucleotide or oligonucleotide according to the present invention can be obtained by various kinds of known techniques for isolating and cloning DNA fragments containing a polynucleotide or oligonucleotide according to the present invention. For example, a probe is prepared that specifically hybridizes with a portion of the base sequence of a polynucleotide of the present invention, and a genomic DNA library or cDNA library is screened with the probe. The probe may have any sequence and/or length as long as it specifically hybridizes with at least a portion of the base sequence, or its complementary sequence, of a polynucleotide of the present invention.

Alternatively, a polynucleotide according to the present invention can be obtained by amplification means such as PCR. For example, PCR amplification may be performed with the step of preparing primers from the 5' and 3' ends of the sequence, or its complementary sequence, of the cDNA of a polynucleotide according to the present invention; and the step of amplifying the DNA with the primers by PCR or other means, using the genomic DNA (or cDNA) as a template, so as to amplify the DNA region between the primers. In this way, DNA fragments containing a polynucleotide according to the present invention can be obtained in mass quantity.

A source of a polynucleotide according to the present invention is not particularly limited, but it is preferably a biological material including a desired polynucleotide. Particularly preferable is *Bryopsis maxima*, from which a polypeptide according to the present invention derives. However, the type of biological material is not just limited to this example.

An object of the present invention is to provide a polynucleotide encoding a polypeptide according to the present invention, and an oligonucleotide that hybridizes with the polynucleotide. As such, a polynucleotide or oligonucleotide according to the present invention is not bound to the foregoing description concerning the specific methods of producing polynucleotides or oligonucleotides, for example. It should therefore be appreciated that the technical scope of the present invention also encompasses a polynucleotide encoding a polypeptide according to the present invention, produced by other methods.

(3) Antibody

The present invention provides an antibody that specifically binds to a polypeptide according to the present invention. As used herein, the term "antibody" refers to immunoglobulins (IgA, IgD, IgE, IgY, IgG, IgM, and Fab fragments, F(ab')2 fragments, and Fc fragments thereof), non-limiting examples of which include polyclonal antibodies, monoclonal antibodies, single-chain antibodies, anti-ideotype antibodies, and humanized antibodies. An antibody according to the present invention may be useful for the selection of biological materials expressing a polypeptide according to the present invention. An antibody according to the present invention is also useful for the purification of the peptide from a crude solution containing a polypeptide according to the present invention.

The "antibody" may be obtained according to various conventional methods, for example, such as Harlow et al.; Antibodies: A laboratory manual (Cold Spring Harbor Laboratory, New York (1988), and Iwasaki et al.; Monoclonal antibody, hybridoma and ELISA, Kodansha (1991).

A peptide antibody may be produced by methods known in the art (for instance, Chow, M., et al., Proc. Natl. Acad. Sci. USA 82:910-914; and Bittle, F. J., et al., J. Gen. Virol. 66:2347-2354 (1985)) (herein incorporated by reference). Generally, animals may be immunized with free peptide; however, anti-peptide antibody titer may be boosted by coupling of the peptide to a macromolecular carrier, for example, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 µg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As used herein, an "antibody that specifically binds to a polypeptide according to the present invention" includes intact antibody molecules, and antibody fragments (for example, Fab and F(ab')2), that can specifically bind to a polypeptide antigen according to the present invention. Fab and F(ab')2 fragments lack the Fc fragment of intact antibody, clear more rapidly from the circulation, and have almost no non-specific tissue binding of an intact antibody (Wahl et al., J. Nucl. Med. 24:316-325 (1983)) (herein incorporated by reference). Thus, such fragments are also preferable.

Alternatively, additional antibodies capable of binding to the peptide antigen of a polypeptide according to the present invention may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, the antibody that specifically binds to a polypeptide according to the present invention is used to immunize an animal, preferably a mouse. The splenocytes of such an animal are then used to produce hybridoma cells, and the hybridoma cells are screened to identify clones which produce an antibody whose ability to specifically bind to a polypeptide according to the present invention can be blocked by a polypeptide antigen according to the present invention. Such antibodies comprise anti-idiotypic antibodies to the antibody that specifically binds to a polypeptide according to the present invention and can be used to immunize an animal to induce formation of a further antibody that specifically binds to a polypeptide according to the present invention.

It will be appreciated that Fab and F(ab')2 and other fragments of an antibody of the present invention may be used according to the methods disclosed herein. Such fragments are typically produced by proteolytic cleavage, using enzymes such as papain (to produce Fab fragments) or pepsin (to produce F(ab')2 fragments). Alternatively, fragments binding to a polypeptide according to the present invention can be produced through the application of recombinant DNA technology or through synthetic chemistry.

As described above, antibodies according to the present invention at least include antibody fragments (for example, Fab and F(ab')2), that recognize a polypeptide according to the present invention. Therefore, it should be appreciated that the present invention also includes immunoglobulins that comprise (i) antibody fragments that recognize a polypeptide according to the present invention, and (ii) Fc fragments of different antibody molecules.

More specifically, since an object of the present invention is to provide antibodies that recognize a polypeptide according to the present invention, the invention is not limited to the specific types of immunoglobulins (IgA, IgD, IgE, IgY, IgG, or IgM), or the specific methods of producing chimeric antibodies and peptide antigens, etc. Therefore, it should be appreciated that antibodies that are obtained by methods other than those described above also fall within the scope of the present invention.

(4) Use of Polypeptide and/or Polynucleotide According to the Present Invention (4-1) Vector The present invention provides a vector used to produce a polypeptide according to the present invention. A vector according to the present invention may be a vector used for in vitro translation, or a vector used for recombination expression.

A vector according to the present invention is not particularly limited as long as it includes a polynucleotide according to the present invention. An example is a recombinant expression vector to which cDNA of a polynucleotide encoding a polypeptide according to the present invention has been introduced. A method for producing the recombinant expression vector is not particularly limited. Methods using plasmids, phages, or cosmids may be used.

The vector is not limited to a specific type of vector, and those that can be expressed in host cells may be suitably selected. Specifically, according to the type of host cell, a suitable promoter sequence for reliable expression of a polynucleotide according to the present invention is selected, and a polynucleotide according to the present invention is incorporated in various kinds of plasmids to provide an expression vector.

Preferably, the expression vector includes at least one selection marker. Examples of such markers include dihydrofolate reductase or neomycin resistant gene for eukaryotic cell culture, and tetracyclin resistant gene or ampicillin resistant gene for *E. coli* and other bacteria.

The selection marker allows for confirmation whether a polynucleotide according to the present invention has been introduced into the hose cell or successfully expressed in the host cell. Alternatively, a polypeptide according to the present invention may be expressed as a fusion polypeptide. For example, green fluorescent polypeptide GFP (green fluorescent protein) derived from *Aequorea victoria* may be used as a marker to express a polypeptide according to the present invention as a GFP-fused polypeptide.

The type of host cell is not particularly limited, and various types of conventional cells may be suitably used. Specific examples include: bacteria such as *Escherichia coli*; yeasts such as *Saccharomyces cerevisiae* and *Schizosaccharomyces pombe*; nematodes such as *Caenorhabditis elegans*; and oocytes of platanna (*Xenopus laevis*). Appropriate culture media and conditions for the above-described host cells are known in the art.

A method of introducing the expression vector into the host cell, i.e., transformation method is not particularly limited either. For example, various types of conventional methods such as an electroporation method, calcium phosphate method, a liposome method, and DEAE dextran method can be suitably used. When a polypeptide according to the present invention is expressed in insects for example, an expression system using baculovirus is used.

In short, a vector according to the present invention at least includes a polynucleotide encoding a polypeptide according to the present invention. That is, vectors other than the expression vector also fall within the technical scope of the present invention.

That is, an object of the present invention is to provide a vector including a polynucleotide encoding a polypeptide according to the present invention. As such, the present invention is not bound to the specific types of vectors and cells, or the specific methods of producing the vector or introducing the vector into cells described above. It should therefore be appreciated that the technical scope of the present invention also encompasses vectors and methods of producing vectors other than those described above.

(4-2) Transformants or Cells

The present invention provides transformants or cells to which a polynucleotide encoding a polypeptide according to the present invention has been introduced. As used herein, the term "transformants" refers to not just tissues or organs but individual organisms themselves.

A method of preparing (producing) transformants or cells is not particularly limited. For example, a host cell may be transformed by introducing the recombinant expression vector described above. The organisms to be transformed are not particularly limited, and may be microorganisms, plants, or animals as exemplified above.

Further, transformants or cells according to the present invention are preferably algae, offspring thereof, or tissues derived therefrom. *Bryopsis maxima* are particularly preferable.

A transformant including a polynucleotide encoding a polypeptide according to the present invention may be obtained by introducing a recombinant vector, having incorporated therein the polynucleotide, into a host cell where the gene can be expressed.

The following explanation will be given through the case where the host cells are plants. However, the host cells used in the present invention are not limited to plants. The recombinant expression vector used for the transformation of plants is not particularly limited as long as it can express a polynucleotide according to the present invention in the plants. Examples of such a vector include a vector with a promoter (for example, cauliflower mosaic virus 35S promoter) for constitutively expressing genes in a plant cell, and a vector with a promoter that is inductively activated in response to external stimuli.

The plants to be transformed in the present invention may be any of the following: whole plants; plant organs (for example, leaf, petal, stem, root, seed, etc.); plant tissues (for example, epidermis, phloem, parenchyma, xylem, fibrovascular bundle, palisade tissue, cancellous tissue, etc.), plant culture cells; and various types of plant cells (for example, suspended culture cells), protoplasts, leaf slices, and calluses. The plant used for transformation is not particularly limited, and it may be a monocot or dicot.

The gene may be introduced into a plant by a transformation method known in the art, for example, such as an *Agrobacterium* method, a particle gun method, a PEG method, and an electroporation method. Among the methods known in the art are, for example, methods mediated by *Agrobacterium*, and methods in which the gene is directly introduced into the plant cells. In using the *Agrobacterium* method, an expression vector constructed for plants is introduced into a suitable *Agrobacterium*, for example, such as *Agrobacterium tumefaciens*, and the resulting strains are used to infect aseptically cultured leaflets according to techniques such as the leaf disc method (Plant Gene Manipulation Manual, Hirofumi UCHIMIYA, 1990, pp. 27-31 Kodansha Scientific, Tokyo), so as to obtain transgenic plants. Further, methods of Nagel et al. (Micribiol. Lett., 67, 325 (1990)) may be used. In this method, an expression vector, for example, is first introduced into *Agrobacterium*, and the *Agrobacterium* so obtained is then introduced into plant cells or tissues according to the method described in Plant Molecular Biology Manual (S. B. Gelvin et al., Academic Press Publishers). As used herein, the "plant tissues" includes calluses obtained by culturing plant cells. In the transformation using *Agrobacterium*, binary vectors (for example, pBI121 or pPZP202) may be used.

Among the known methods for directly introducing the gene into plant cells or tissues are the electroporation method and the particle gun method. In using the particle gun method, it is possible to use plants, plant organs, and plant tissues either directly or in the form of a slice or even a protoplast. The samples so prepared may be processed using a gene introducing device, for example, such as PDS-1000 of BIO-RAD. Processing conditions vary depending on types of plants and samples. Generally, the samples are processed under the pressure of about 450 psi to about 2000 psi, and at the distance of about 4 cm to about 12 cm.

The cells or plant tissues having introduced therein the gene are first selected based on drug resistance such as hygromycin resistance and then reproduced into plants by ordinary methods. Reproduction of plants from the transformed cells may be performed by methods known in the art according to the type of plant cells.

In the case of using cultured plant cells as hosts, the cells are transformed by introducing recombinant vector into the cultured cells using methods such as a particle gun method and an electroporation method. The calluses, shoots, or hairy root obtained by the transformation may be directly used to culture cells, tissues, or organs, or may be reproduced into plants by administration of appropriate concentrations of plant hormones, such as auxin, cytokinin, gibberellin, abscisic acid, ethylene, brassinolide, using known plant tissue culturing methods.

Whether the gene was successfully introduced into the plant may be determined, for example, by a PCR method, a southern hybridization method, and a northern hybridization method. For example, DNA is prepared from transformed plants, and DNA-specific primers are designed for PCR. PCR may be performed under the same conditions as those used for the preparation of the plasmid. The amplified products may be subjected to agarose gel electrophoresis, polyacrylamide gel electrophoresis, capillary electrophoresis or the like, and may be stained with ethidium bromide, SYBR Green solution or the like. Transformation can be confirmed by detecting the amplified product as a single band. Detection of amplified products may also be performed by PCR using primers that have been labeled with a fluorescent dye or the like. The presence of amplified products may also be confirmed by a method in which the amplified products are bound to a solid phase such as a micro plate and are confirmed by fluorescence or enzyme reaction or the like.

Once a transformant plant is obtained that has incorporated a polynucleotide according to the present invention in its genome, offspring of the plant can be obtained by reproducing the plant either sexually or asexually. Further, seeds, fruits, cuttings, tuberous stems, tuberous roots, stumps, callus, and protoplasts may be obtained from the plant, or from its offspring or clones. From these materials, the plant may be mass-produced. The present invention therefore includes plants into which a polynucleotide according to the present invention is expressibly introduced, their offspring having the same characteristics, and tissues derived from the plants or their offspring.

As described above, a transformant or cell according to the present invention at least includes a polynucleotide encoding a polypeptide according to the present invention. That is, transformants or cells produced by means other than using recombinant expression vectors also fall within the technical scope of the present invention.

An object of the present invention is to produce transformants or cells to which a polynucleotide encoding a polypeptide according to the present invention has been introduced. As such, the invention is not limited to the types of vectors and methods of introduction described herein. It should therefore be appreciated that the technical scope of the present invention also encompasses transformants or cells that are produced by using various types of vectors and cells, and various methods of producing vectors and various methods of introduction, other than those described above.

(4-3) Producing Method of Polypeptide

The present invention provides a method for producing a polypeptide according to the present invention.

In one embodiment, a producing method of a polypeptide according to the present invention uses a vector including a polynucleotide encoding a polypeptide according to the present invention.

In one aspect of the embodiment, it is preferable in a producing method of a polypeptide according to the present embodiment that the vector be used for an acellular protein synthesis system. In the case of using an acellular protein synthesis system, various types of commercially available kits may be used. Preferably, a producing method of a polypeptide according to the present embodiment includes a step of incubating the vector and an acellular protein synthesis solution.

In another aspect of the present embodiment, a producing method of a polypeptide according to the present embodiment preferably uses a recombinant expression system. In the case of using a recombinant expression system, a polypeptide may be produced, for example, by a method in which a recombinant expression vector having incorporated therein a polynucleotide according to the present invention is introduced into an expressible host, and in which a polypeptide obtained by the translation in the host is purified. The recombinant expression vector may or may not be a plasmid as long as a polynucleotide of interest is introduced into the host. Preferably, a producing method of a polypeptide according to the present embodiment includes a step of introducing the vector into a host.

When introducing a foreign polynucleotide into a host in this manner, it is preferable that the expression vector has incorporated therein a promoter that becomes functional in the host and causes expression of the foreign polynucleotide. The method of purifying the recombinantly produced polypeptide varies depending on characteristics of the host and polypeptide used. With the use of a tag for example, a polypeptide of interest can be purified with relative ease.

A producing method of a polypeptide according to the present embodiment preferably includes a further step of purifying a polypeptide of the present invention from an extract of cells or tissues including a polypeptide according to the present invention. The step of purifying a polypeptide preferably proceeds with, but is not limited to, preparing a cell or tissue extract by a known method (for example, a method in which a soluble fraction is collected by centrifugation of disrupted cells or tissues), and then purifying the polypeptide from the extractant by a known method, for example, such as ammonium sulfate precipitation or ethanol precipitation, acid extraction, anion or cation exchange chromatography, phosphocellulose chromatography, hydrophobic interaction chromatography, affinity chromatography, hydroxyapattite chromatography, or lectin chromatography. For the purification, high-performance liquid chromatography (HPLC) is most preferably used.

In another embodiment, a producing method of a polypeptide according to the present invention purifies a polypeptide of the present invention from cells or tissues naturally expressing a polypeptide according to the present invention. A producing method of a polypeptide according to the present invention preferably includes a step of identifying cells or tissues naturally expressing a polypeptide according to the present invention, using the antibody or oligonucleotide described above. A producing method of a polypeptide according to the present invention preferably includes a further step of purifying the polypeptide.

In yet another embodiment, a producing method of a polypeptide according to the present invention chemically synthesizes a polypeptide according to the present invention. A person ordinary skill in the art will readily understand that a polypeptide according to the present invention can be chemically synthesized by applying known chemical synthesis techniques based on an amino acid sequence of a polypeptide according to the present invention as described herein.

As noted above, a polypeptide obtained by a producing method of a polypeptide according to the present invention may be a naturally occurring mutant polypeptide, or an artificially produced mutant polypeptide.

A method of preparing a mutant polypeptide is not particularly limited either. For example, a mutant polypeptide may be generated by introducing a point mutation in the base sequence using conventional mutant polypeptide inducing methods, such as a site-directed mutagenesis (see Hashimoto-Gotoh, Gene 152, 271-275 (1995), for example) or PCR. Alternatively, a mutant polypeptide may be generated by a method in which mutant strains are produced by insertion of transposons. Further, a commercially available kit may be used to produce mutant polypeptides.

As described above, a producing method of a polypeptide according to the present invention at least employs known techniques based on an amino acid sequence of a polypeptide according to the present invention, or a base sequence of a polynucleotide encoding a polypeptide according to the present invention.

That is, an object of the present invention is to provide a producing method of a polypeptide according to the present invention. It should therefore be appreciated that the technical scope of the present invention also encompasses producing methods including steps other than those described above.

(4-4) Detecting Instrument

The present invention also provides various types of detecting instruments. A detecting instrument according to the present invention includes a substrate on which a polynucleotide or fragments according to the present invention are immobilized, or a substrate on which a polypeptide and an antibody according to the present invention are immobilized. A detecting instrument according to the present invention is usable, for example, for the detection and measurement of expression patterns of a polynucleotide and polypeptide according to the present invention.

In one embodiment, a detecting instrument according to the present invention includes a substrate on which a polynucleotide and/or oligonucleotide according to the present invention are immobilized. In a preferred aspect of the present embodiment, a detecting instrument according to the present embodiment is a DNA chip.

As used herein, the term "DNA chip" means a synthetic DNA chip in which a synthesized oligonucleotide is immobilized on a substrate. However, the meaning of "DNA chip" is not limited to this and it also includes an adhesion DNA microarray in which PCR products, such as cDNA, are immobilized on a substrate. For example, the DNA chip may be a DNA chip in which a probe (oligonucleotide according to the present invention) that specifically hybridizes with a gene of the present invention is immobilized on a substrate (support). The probe sequence may be determined by a conventional method of specifying a characteristic sequence of cDNA sequences. A non-limiting example of such a method is a SAGE (Serial Analysis of Gene Expression) method, as described in Science 276:1268, 1997; Cell 88: 243, 1997; Science 270: 484, 1995; Nature 389: 300, 1997; U.S. Pat. No. 5,695,937.

The DNA chip may be made by a known method. For example, when a synthetic oligonucleotide is used as the oligonucleotide, it may be synthesized on a substrate by a combination of photolithography and solid phase DNA synthesis technique. On the other hand, when the oligonucleotide is cDNA, it is stuck on a substrate using an array device.

Further, as in common DNA chips, the accuracy of polynucleotide detection can be improved by placing a perfect-match probe (oligonucleotide) and a mismatch probe that has been prepared by substituting a single nucleotide of the perfect-match probe. Further, in order to detect different polynucleotides simultaneously, a DNA chip may be prepared in which different types of oligonucleotides are immobilized on a single substrate.

The material of the substrate used for the detecting instrument according to the present embodiment may be selected from those that allow the polynucleotide or oligonucleotide to be stably immobilized. Other than the foregoing example, synthetic resin such as polycarbonate or plastic, or glass may be used, for example. However, the material of the substrate is not just limited to these examples. The form of substrate is not particularly limited either. For example, a substrate in the form of a plate or a film may be suitably used. In a preferred aspect of the embodiment, the detecting instrument of the embodiment is used for the detection in which the cDNA library constructed from various kinds of organisms, or tissues or cells thereof, is used as a target sample.

In another embodiment, a detecting instrument according to the present invention includes a substrate on which a polypeptide or an antibody according to the present invention is immobilized. In a preferred aspect of the embodiment, the detecting instrument according to the embodiment is a protein chip.

As used herein, the term "substrate" is intended a substance that can support a target substance, for example, such as a polynucleotide, oligonucleotide, polypeptide, or protein, and the term is used interchangeably with "support." The substrate (support) is preferably, but is not limited to, beads (for example, polystyrene beads), or a solid phase (for example, glass tube, reagent strip, polystyrene micro titer plate, or amino acid binding micro titer plate). The method of immobilizing the target substance on the substrate is known to skilled artisan, and is described in, for example, Nature, 357: 519-520 (1992), which is herein incorporated by reference.

The material of the substrate used for the detecting instrument according to the present embodiment may be selected from those that allow the polypeptide or antibody to be stably immobilized. Other than the foregoing example, synthetic resin such as polycarbonate or plastic, or glass may be used, for example. However, the material of the substrate is not just limited to these examples. The form of substrate is not particularly limited either. For example, a substrate in the form of a plate or a film may be suitably used.

Other than the foregoing method, the polypeptide or antibody may be immobilized on the substrate, for example, by a physical adsorption method, in which the polypeptide or antibody is spotted on a nitrocellulose film or a PDVF film in the manner employed in dot blotting, or by a method in which the polypeptide or antibody is spotted on polyacrylamide pads that have been attached to a glass slide in order to reduce denaturation of the polypeptide or antibody. In the case where not only adsorption but strong binding of the polypeptide or antibody to the substrate surface is needed, the method using an aldehyde-modified glass (G. MacBeath, S. L. Schreiber, Science, 289, 1760 (2000)) may be used. In the case where the polypeptide is to be immobilized on the substrate by being aligned thereon, a method may be used in which the polypeptide is immobilized, via an oligohistidine tag, on a substrate that has been surface-modified with a nickel complex (H. Zhu, M. Bilgin, R. Bangham, D. Hall, A. Casamayor, P. Bertone, N. Lan, R. Jansen, S. Bidlingmaier, T. Houfek, T. Mitchell, P. Miller, R. A. Dean, M. Gerstein, M. Snyder, Science, 293, 2102 (2001)).

In a preferred aspect of the embodiment, the detecting instrument according to the embodiment is used for the detection in which the extract obtained from various kinds of organisms, or tissues or cells thereof, is used as a target sample.

As described above, a detecting instrument according to the present invention is an instrument in which at least a polynucleotide or oligonucleotide according to the present invention, or a polypeptide according to the present invention or an antibody that binds to a polypeptide according to the present invention is immobilized on a support. In other words, a detecting instrument according to the present invention includes a substrate on which a polynucleotide or oligonucleotide according to the present invention, or a polypeptide according to the present invention or an antibody that binds to a polypeptide according to the present invention is immobilized. It should therefore be appreciated that the technical scope of the present invention also encompasses cases where the detecting instrument includes constituting members other than such supports (and substrates).

That is, an object of the present invention is to provide an instrument for detecting a polypeptide or polynucleotide according to the present invention, or a polypeptide that binds to an antibody according to the present invention. As such, the invention is not just limited to the specific types of supports and the specific methods of immobilization described herein. It should therefore be appreciated that a detecting instrument including constituting members other than the support also falls within the scope of the present invention.

(4-5) Purification of Antibody Using Polypeptide According to the Present Invention Antibodies purified by the present invention may be any antibodies, including antiserum obtained by immunizing animals with antigens, monoclonal antibodies secreted by hybridoma cells prepared from the splenic cells of animals immunized with antigens, and antibodies prepared by gene recombination techniques, i.e., antibodies obtained from host cells to which an antibody expression vector having incorporated therein an antibody gene has been introduced. A fusion protein fused with Fc region of antibody is also regarded as an antibody in the present invention. Preferable as a purified antibody is chicken antibody. This is because a polypeptide according to the present invention has high affinity to the sugar chain binding to the chicken antibody. The chicken antibody includes antibodies (IgY, IgE, etc.) produced by chicken immunized with antigens, and antibodies produced by animals other than chicken and having the same structure as the antibodies derived from chicken. The antibody may be monoclonal antibody or polyclonal antibody. For details of the antibody, reference should be made to the description in Section (3) below concerning antibody.

A purification method of an antibody according to the present invention is achieved, for example, by chromatography using a support on which a polypeptide according to the present invention is immobilized. Examples of a support on which a polypeptide according to the present invention is immobilized include agarose, and a polymer of acrylic synthetic resin, and, preferably, a polymer of acrylic ester. Other than these examples, various affinity supports may be suitably selected from commercially available products, which include, for example, HiTrap NHS-activated HP columns (Amersham Bioscience Corp), and CNBr-activated Sepharose 4 Fast Flow Lab Packs (Amersham Bioscience Corp). In the case where a high-performance liquid chromatography (hereinafter "HPLC") system is used, any commercially available HPLC system may be used. For example, LC-6A of Shimadzu may be used. As to the method of immobilization, an optimum method may be suitably selected according to the type of support.

The following describes an example of a purification method using a HPLC system. As the eluent, 10 to 100 (mmol/l) of tris-hydrochloric acid buffer, or 10 to 100 (mmol/l) of phosphate buffer is used, for example. A preferable pH range is about 7 to 8. First, a column is sufficiently equilibrated with initial buffer such as 10 to 100 (mmol/l) tris-hydrochloric acid buffer or 10 to 100 (mmol/l) phosphate buffer. A sample is then passed through the HPLC system and eluted with 10 to 100 (mmol/l) tris-hydrochloric acid buffer or 10 to 100 (mmol/l) phosphate buffer containing eluting sugar. The sugar used for the elution may be suitably selected. When a polypeptide according to the present invention is immobilized, 0.02 to 0.5 mol/l D-mannose or 0.02 to 0.5 mol/l methyl-$\alpha$-D-mannoside is used. Elution is performed by a stepwise method or a gradient method. The protein (antibody) may be detected by a method, for example, such as ultraviolet absorption, electrophoresis (SDS-PAGE, etc.), ELISA method, or western blot method.

A purification method of an antibody according to the present invention may also be achieved by using Carnin, a conventionally known lectin, instead of or in addition to a polypeptide according to the present invention. In order to achieve the foregoing objects, a purification method of an antibody according to the present invention may be a method using a polypeptide according to the present invention, a method using Carnin in addition to a polypeptide according to the present invention, or a method using one of or both of a polypeptide according to the present invention and Carnin.

Likewise, a support according to the present invention may be one on which a polypeptide according to the present invention is immobilized, one on which Carnin is immobilized in addition to a polypeptide according to the present invention, or one on which one of or both of a polypeptide according to the present invention and Carnin are immobilized. Description concerning Carnin derived from algae (*Carpopeltis flabellata=C. prorifera*) is found in "Hori, K., Matsuda, H., Miyazawa, K. and Ito, K.: A mitogenic agglutinin from the red alga *Carpopeltis flabellata*. Phytochemistry, 26, 1335-1338 (1987)," which is hereby incorporated by reference.

The following will describe the present invention in more detail by way of Examples. The present invention, however, is not limited by the following description.

EXAMPLES

Example 1

Isolation of Polypeptide (BML-17) from Algae (*Bryopsis maxima*)

(Preparation of Extracts and Ammonium Sulfate Precipitation)

To 12.2 g of a freeze-dried powder of *Bryopsis maxima* was added 200 ml of 20 mM PBSA (phosphate-buffered saline containing 0.2% sodium azide, pH 7.0). The mixture was stirred overnight at 4° C., and this was followed by centrifugation to obtain an extract solution. The procedure was repeated 3 times to obtain extract solutions 1 to 3.

An ammonium sulfate powder was then slowly added to each extract solution to a 20% saturation, and the mixture was allowed to stand overnight at 4° C. The precipitate obtained by centrifugation (10,000 rpm, 30 minutes) was dissolved in PBSA, and was sufficiently dialyzed with the solvent. After dialysis, the internal solution was centrifuged and the resulting supernatant was obtained as a 20%-saturated ammonium sulfate-precipitate fraction. The supernatant obtained by the precipitation procedure with a 20%-saturated ammonium sulfate was supplemented with an ammonium sulfate powder to attain a 60% saturation, and the mixture was processed in the same manner to obtain a 20 to 60%-saturated ammonium sulfate-precipitate fraction.

(Evaluation of Agglutinating Activity)

Hemagglutinating activity was measured using a micro titer method. Twenty-five µl of serially two-fold dilutions of each purified fraction solution adjusted with saline was placed on a micro titer plate. Each diluted solution was supplemented with 25 µl of a 2% suspension of trypsin-treated rabbit erythrocytes and was gently stirred. The mixture was allowed to stand at room temperature for 1.5 hours and agglutination was observed. Agglutination was evaluated with naked eye. Agglutination of 50% or greater percentage of red blood cells was evaluated as positive. Agglutinating activity was given by agglutination titer, i.e., the protein concentration of maximum diluent showing agglutinating activity.

In this Example, trypsin-treated rabbit red blood cells (TRBC) were used as red blood cells. TRBC was prepared as follows. First, 2 ml of blood was collected from the ear of a rabbit kept in laboratory. The blood sample was washed 3 times with about 50 ml of saline, and was supplemented with 50 ml of saline to obtain a 2% rabbit blood cell suspension. The solution was supplemented with ⅒ volume of 0.5% trypsin in saline, and was allowed to stand at 37° C. for 1.5 hours. The trypsin-treated red blood cells were then washed 3 times with saline, and were supplemented with 45 ml of saline to obtain a 2% suspension of trypsin-treated rabbit erythrocytes (or blood cells) (TRBC).

As a result of assessment of active component of agglutination for TRBC, the agglutinating activity was detected in extract solutions 1 to 3. The total agglutinating activity (THA) and the soluble protein content of extract solution 1 were higher than those of extract solutions 2 and 3, showing that a large proportion of the agglutinating activity component was collected in extract solution 1. It was also found that large proportions of THA and soluble protein were collected in the precipitates with 20 to 60%-saturated ammonium sulfate.

(Gel Filtration)

The 20 to 60%-saturated ammonium sulfate-precipitates from extract solution 1 were applied to a gel filtration column (TOSOH, Toyopearl HW-55 column, 4.4×900 cm, Vt=1368 ml). Specifically, 16 ml of the precipitated fraction was introduced into Toyopearl HW-55 column equilibriated with 20 mM PBSA (pH 7.0), and was eluted with PBSA at a flow rate of 60 ml/h. Fifteen ml each of eluate was collected, and UV 280 nm and agglutinating activity of each fraction were measured.

(Hydrophobic Chromatography)

A 110 ml portion of active fractions obtained by gel filtration was dialyzed against. 20 mM tris-hydrochloric acid buffer (pH 7.0) containing 0.86 M ammonium sulfate. The non-dialyzed solution (80 ml) so obtained was applied to TSKgel Phenyl-5PW column (7.5×75 mm) that had been equilibriated with the same buffer. Elution was performed by a linear gradient elution method between 20 mM tris-hydrochloric acid buffer, pH 7.0 (solvent A) and the same buffer containing 0.86 M ammonia sulfate, pH 7.0 (solvent B). The concentration gradient [solvent B 100% (20 minutes), solvent B 0%-solvent A 100% (20 to 60 minutes), solvent A 100% (60 to 90 minutes)] was set using a gradient programmer (CCP controller, TOSOH). The flow rate was 0.5 ml/min. The eluate was monitored at UV 280 nm. Each peak was collected and agglutinating activity was measured.

(SDS-PAGE)

The fraction (purified fraction) with agglutinating activity obtained by hydrophobic chromatography was subjected to SDS-PAGE (10% gel).

The results are shown in FIG. 7. Lane 1 represents molecular weight markers (94 kDa, 67 kDa, 43 kDa, 30 kDa, 20.1 kDa, and 14.4 kDa bands from the top). Lane 2 represents a purified fraction under non-reducing conditions (without 2-mercaptoethanol treatment). Lane 3 represents a purified fraction under reducing conditions (with 2-mercaptoethanol treatment). Lane 4 represents molecular weight markers (16.9 kDa, 14.4 kDa, 10.7 kDa, 8.2 kDa, 6.2 kDa, and 2.5 kDa bands from the top). Proteins were stained with CBB (Coomassie brilliant blue R-250).

As can be seen from FIG. 7, the purified fraction in SDS-PAGE gave a single band with a relative molecular weight of about 17 kDa under non-reducing conditions, and a single band of 18 kDa under reducing conditions. The different molecular weights under reducing and non-reducing conditions suggested the presence of intrachain disulfide bond (S—S bond) in the same purified fraction. The purification process finally gave 2.1 mg of purified fraction. The inventors of the present invention denominated the purified fraction as "BML-17."

(Evaluation of Molecular Weight of BML-17)

BML-17 and pyridylethylated (PE)-BML-17 were subjected in 0.1% TFA-70% acetonitrile solution and the solution was subjected to electrospray ionization mass spectrometry (ESI-MS, LCQ, Finigan) to measure molecular weight.

PE treatment was performed according to the following procedure. BML-17 (200 µg) was dissolved in a 100 µl buffer (0.25 M tris-hydrochloric acid buffer containing 6M guanidine hydrochloride and 1 mM EDTA, pH 8.5). The solution was supplemented with 200 µg of dithiothreitol, and the vessel was flushed with nitrogen and was allowed to stand for 2 hours. The solution was then well mixed with 2 µl of 4-vinylpyridine (nacalai tesque) and thoroughly stirred. The mixture was allowed to stand overnight in dark to sufficiently facilitate reaction, and was dialyzed with ultrapure water to remove salts and excess reagents. The resulting internal solution was denominated as "pyridylethylated (PE) BML-17."

From the results of SDS-PAGE, a relative molecular weight of BML-17 was estimated to be about 17 kDa under non-reducing conditions, and 18 kDa under reducing conditions. The ESI-MS measurement gave a molecular weight of 17,293 Da. The molecular weight of PE-treated BML-17 was 17,945 Da. Since the difference between these molecular weights substantially corresponds to the molecular weight of 6 pyridylethyl groups, BML-17 was estimated to include 6 cysteine residues.

(Analysis of Amino Acid Composition of BML-17)

Analysis of amino acid composition of BML-17 was performed using a dabsylation method. For the analysis, PE-treated BML-17 was used.

The result of analysis revealed the amino acid composition of BML-17 as follows: 11.8 mol % asparagine or aspartic acid (Asx); 6.8 mol % glutamine or glutamic acid (Glx); 9.6 mol % serine (Ser); 6.0 mol % threonine (Thr); 11.4 mol % glycin (Gly); 7.9 mol % alanine (Ala); 3.4 mol % proline (Pro); 6.9 mol % valine (Val); 3.9 mol % arginine (Arg); 2.7 mol % methionine (Met); 4.5 mol % isoleucine (Ile); 4.4 mol % leucine (Leu); 3.7 mol % phenylalanine (Phe); 4.6 mol % lysine (Lys); 2.6 mol % histidine (His); 4.9 mol % tyrosine (Tyr); and 3.4 mol % tryptophan (Trp). No analysis was made for cysteine (Cys).

The result showed that BML-17, like known lectins, contained large amounts of glycine and acidic amino acids. Serine was also abundant in BML-17.

(Analysis of N-Terminal Amino Acid of BML-17)

The amino acid sequence at the N terminal of BML-17 was analyzed using an automated analyzer: Edman Protein Sequencer (Type G1005A) of Hewlett-Packard. For the analysis of N-terminal amino acid, BML-17 was used in the amount equivalent to 100 pmol.

FIG. 8 shows the amino acid sequence at the N-terminal of BML-17 ("BML"), along with N-terminal amino acid sequences of previously isolated *Bryopsis* lectins (BCL, BPL, Bry-1, Bry-2). As shown in FIG. 8, the N-terminal amino acid sequence of BML-17 was completely different from its counterpart in known lectins derived from *Bryopsis*, suggesting that BML-17 was a totally novel lectin. The N-terminal amino acid sequences of BML-17, BCL, BPL, Bry-1, and Bry-2 are represented by SEQ ID NOs: 13, 14, 15, 16, and 17, respectively.

(Temperature Stability and pH Stability of BML-17)

Temperature stability and pH stability of BML-17 were evaluated, using agglutinating activity for trypsin-treated rabbit red blood cell (TRBC) as a measure.

The agglutinating activity of BML-17 attenuated at 60° C. and greater temperatures and by a 30-minute heat treatment, revealing that heat resistance of BML-17 was relatively poor. The agglutinating activity was stable at pH 4.0 to pH 11.0.

(Divalent Metal Ion Requirement of BML-17)

Agglutinating activity of BML-17 did not alter after EDTA treatment. Further, the fact that the addition of divalent metal ions did not alter the agglutinating activity of the EDTA-treated solution revealed that BML-17 did not require divalent metal ions for the expression of agglutinating activity.

(Hemagglutination-Inhibition Test)

Hemagglutination-inhibition test was performed according to the following procedure. First, each 25 µl of serially two-fold dilutions of sugar solution in saline was placed on a micro titer plate. The concentration of the original solutions of sugars examined was 100 mM for monosaccharides and oligosaccharides, and 2 mg/ml for glycoproteins. Each solution was mixed with 25 µl of BML-17 solution that had been adjusted to an agglutination titer of 4, and allowed to stand for 1.5 hours at room temperature after gentle stirring. Then, 25 µl of TRBC was added, and the mixture was allowed to stand for 2 hours at room temperature to observe hemagglutination inhibitory capability. The presence or absence of hemagglutination inhibitory capability was determined by naked eye. The test was positive when no hemagglutination occurred in about 100% of the red blood cells. Hemagglutination inhibitory capability (hemagglutination inhibitory activity) was denoted by a minimum inhibitory concentration of a sugar, i.e., the minimum concentration (mM or mg/ml) at which hemagglutination inhibitory capability is exhibited.

The hemagglutination inhibition test used D-glucose, D-galactose, D-mannose, N-acetyl-D-glucosamine, N-acetyl-D-galactosamine, D-xylose, L-fucose, fructose, lactose, and raffinose as monosaccharides and oligosaccharides. As glycoproteins, mucin (bovine submaxillary gland) and asialomucin, fetuin (type III, calf serum) and asialofetuin, transferrin (human) and asialotransferrin, α1-acid glycoprotein (human) and alialo-α1-acid glycoprotein, and yeast mannan were used.

The results are shown in Table 2. Agglutinating activity of BML-17 was inhibited by D-mannose among monosaccharides. No inhibition occurred with disaccharides. Among glycoproteins, inhibition occurred with transferrin, fetuin, mucin (asialotransferrin, asialofetuin, asialomucin), and yeast mannan. The inhibitory action of the glycoproteins was stronger in asialo form than in sialo form except for mucin. Yeast mannan had the strongest inhibitory action. These results suggest that BML-17 has high affinity to the high-mannose-type sugar chain of N-glycosidic-type sugar chains.

(Binding Assay for Sugar Chains)

As the test sugar chains, 44 kinds of pyridylamino sugar chains (hereinafter, "PA sugar chains") were used. 12 kinds of complex type, 13 kinds of high-mannose-type, 3 kinds of hybrid type, a common core structure and its relatives, 8 kinds of glycolipid sugar chain, 5 kinds of oligomannose, and PA-mannose. The structures of sugars tested (Nos. 1-44) are shown in Tables 3 and 4. All the PA sugar chains were obtained from commercially available products (TAKARA BIO INC., Ajinoki) except for PA-oligomannose, which was synthesized by the inventors of the present invention.

The binding assay for sugar chains was performed using a centrifugal ultrafiltration method as follows. Ninety µl of 500 nM BML-17 solution (45 pmol) and 10 µl of 300 nM PA sugar chain solution (3 pmol) in 50 mM tris-hydrochloric acid buffer (pH 7.0) were gently mixed together, and the mixture was kept at room temperature for 60 minutes. The reaction mixture was then subjected to centrifugal filtration (10,000 g, 30 seconds) using a microcentrifugal ultrafilter (NanoSpin-Plus, fraction molecular weight 10,000, GelmanScience), and 20 µl of filtrate was subjected to HPLC. The amount of PA sugar chain in the filtrate was measured as the amount of free sugar chain. Thereafter, 90 µl of 50 mM tris-hydrochloric acid buffer (pH 7.0) and 10 µl of PA sugar chain aqueous solution were mixed together and were processed in the same manner as above. Then, 20 µl of filtrate was subjected to HPLC, and the amount of PA sugar chain in the filtrate was measured as the amount of added sugar chain. The amount of sugar chain that bound to BML-17 was calculated by subtracting the amount of free sugar chain after the reaction from the amount of sugar chain added. The binding activity of BML-17 for the sugar chain was given as a ratio (%) of the amount of bound sugar chain to added sugar chain. Note that, the binding assay for sugar chains was performed twice for each sugar chain, and the mean value was taken as the sugar chain binding activity.

The results are shown in FIG. 5. The numbering 1 to 44 under the column "Oligosaccharide" correspond to the numbers assigned to the respective test sugars listed in Tables 3 and 4.

As can be seen from Table 5, BML-17 had strong binding activity for the high-mannose-type sugar chains (18 to 28). The binding activity for the high-mannose-type sugar chains was the highest for the sugar chain (20) that had the greatest number of α1-2 mannose (hereinafter, "α1-2 Man") residues at the non-reducing ends. However, binding occurred irrespective of the presence or absence of "α1-2 Man" at the non-reducing end. BML-17 also bound to the common core structure (13) and L-Fuc-containing common core structure (14) of the N-glycosidic-type sugar chains, and, though weak, to the free mannopentasaccharide (35) at the branched sugar chain portion. However, no binding occurred with free trimannose (34) or mannodisaccharide (31 to 33) constituting the common core structure or branched sugar chains. Further, from the comparison of binding activity between the sugar chains 13 (binding activity, 19.8%) and 34 (binding activity, 0%), or sugar chains 18 (binding activity, 32.7%) and 35 (binding activity, 14.2%), it was found that the GlcNAcβ1-4GlcNAc moiety at the reducing end also played a supplementary role in the binding, even though the branched sugar chain was recognized. Further, from the comparison of binding activity between the sugar chain 28 (binding activity, 19.1%) and the sugar chain 29 (binding activity, 0%) or 30 (binding activity, 0%), it was found that the binding of BML-17 to the high-mannose-type sugar chains required the minimum sugar chain structure, i.e., the sugar chain (28) with the Man α1-6 (Man al-3) residue attached to the Man α1-6 arm of the common core structure. Weak binding activity was also observed in the complex type sugar chains (1, 5, 6, 10). This suggests the possibility that BML-17 may also recognize the common core structure of N-glycosidic sugar chains, though may be weak.

None of the high-mannose-type sugar chain-specific lectins that have been so far purified from seaweed binds to mannose or other monosaccharides, oligomannose, and the common core structure of the high-mannose-type sugar chains. All of these lectins recognize the branching portions of the high-mannose-type sugar chain and are divided into the following two categories: those showing strong binding activity for sugar chains that have no α1-2 Man residue at the non-reducing end; and those showing binding activity only for sugar chains that have α1-2 Man residue at the non-reducing end. Despite the binding specificity for the high-mannose-type sugar chains, BML-17 also shows weak affinity to the core structure and oligomannoses, and forms the bond irrespective of the presence or absence of the α1-2 Man residue at the non-reducing end. This makes BML-17 as a novel lectin, different from any known lectins specific to the high-mannose-type sugar chains. BML-17 therefore has great applicability as a novel sugar chain probe.

Interestingly, the agglutinating activity of the active fractions obtained by gel filtration was not inhibited at all by D-Man and yeast mannan, and the presence of ConA-binding glycoprotein(s) was confirmed in these fractions by western blotting. This suggests the possibility that the lectin protein may assemble with the coexisting glycoproteins containing the high-mannose-type sugar chains, and may dissociate only in hydrophobic environment.

Generally stated, lectins are divalent or multivalent nonimmunological carbohydrate-binding proteins that are found in animals, plants, and bacteria. They agglutinate animal and plant cells, precipitate polysaccharides and complex carbohydrates. The binding specificity of lectins can be defined by agglutination or precipitation inhibition test or the like using monosaccharides or oligosaccharides.

Example 2

Cloning of BML-17 cDNA cDNA of BML-17 was cloned from cDNA library according to the following procedure. Unless otherwise noted, the procedure was performed under standard conditions. Where applicable, various kinds of kits were used according to the procedures described in the manuals attached to the kits.

Total RNA was extracted from *Bryopsis maxima* culture using AGPC method (Acid Guanidiumu-Phenol-Chloroform method), and mRNA was purified with Oligotex™-dt30 mRNA Purification Kit (TAKARA BIO INC.).

Then, double stranded cDNA was synthesized using RT-PCR and was introduced into plasmid vector pBSK(+)/E/N (STRATAGENE). The plasmid vector was then introduced into competent cells (*E. coli* DH10B) with ElectroMaxDH10B (GIBCO BRL) to construct cDNA library.

Next, degenerate primers were designed based on information of amino acid sequences in the N-terminal region of BML-17. Degenerate primer SP1-17 was designed based on the amino acid sequence (DMFAKIPMPGH: SEQ ID NO: 3) of the 10$^{th}$ to 20$^{th}$ residues in the N-terminal region of BML-17. Degenerate primer SP2-17 was designed based on the amino acid sequence (AKGMVEAY: SEQ ID NO: 4) of the 46$^{th}$ to 54$^{th}$ residues in the N-terminal region of BML-17. Degenerate primer SP3-17 was designed based on the amino acid sequence (YQDPVTSDMFE: SEQ ID NO: 5) of the 3$^{rd}$ to 13$^{th}$ residues in the N-terminal region of BML-17.

```
SP1-17 has the base sequence
GACATGTTCGCNAAGATYCCNATGCCNGGNCA.      (SEQ ID NO: 6)

SP2-17 has the base sequence
GTACGCCTCGACCACCACGCCCTTAGCATCCA.      (SEQ ID NO: 7)

SP3-17 has the base sequence
CCAAGACCCCGTAACTTCAGATATGTTCG.         (SEQ ID NO: 8)
```

By 3' RACE performed with primer AP2 designed from the base sequences of SP1-17 and the vector, 3' unknown region was determined.

By 5' RACE performed with primer AP3 designed from the base sequences of SP2-17 and the vector, 5' unknown region was determined.

Nested PCR was performed using SP3-17 and AP3.

```
AP2 has the base sequence
AACCCTCACTAAAGGGAACAAAAGCTGGA.         (SEQ ID NO: 9)

AP3 has the base sequence
TTGTAATACGACTCACTATAGGGCGA.            (SEQ ID NO: 10)
```

The resulting PCR products were purified with low-melting-point agarose, and subcloning was performed using pGEM-T Easy Vector System (PROMEGA). Purified plasmids were collected from the clones, and base sequences were determined by a dideoxy method.

FIG. 2 represents the base sequence of BML-17 cDNA, and the amino acid sequence determined from the base sequence. It was found that the cloned BML-17 cDNA encoded part of the signal peptide of 23 amino acid residues (surrounded by solid lines in FIG. 2), and the polypeptide of 168 amino acid residues. The total base sequence of the cloned cDNA is represented by SEQ ID NO: 11, and an estimated amino acid sequence is represented by SEQ ID NO: 12. The base sequence of BML-17 is represented by SEQ ID NO: 1, and the estimated amino acid sequence is represented by SEQ ID NO: 2.

Example 3

Search for Lectins that Bind to Chicken Egg Yolk Antibody (Chicken IgY Antibody)

(Test Lectins)
Algae-(seaweed)-derived lectins: *Eucheuma serra*-derived lectin ESA-2 (see Kawakubo, A., Makino, H., Ohnishi, J., Hirohara, H. and Hori, K.: The marine red alga *Eucheuma serra* J. Agardh, a high yielding source of two isolectins. J. Appl. Phycol., 9, 331-338 (1997)), *Solieria robusta*-derived lectin Solnin B (see Hori, K., Ikegami, S., Miyazawa, K. and Ito, K.: Mitogenic and antineoplastic isoagglutinins from the red alga *Solieria robusta*. Phytochemistry, 27, 2063-2067 (1988)), *Boodlea coacta*-derived lectin BCL (see Hori, K., Miyazawa, K., and Ito, K.: Isolation and characterization of glycoconjugate-specific isoagglutinins from a marine green alga *Boodlea coacta* (Dickie) Murray et De Toni. Bot. Mar., 29, 323-328 (1986)), *Carpopeltis flabellata*-derived lectin Carnin (see Hori, K., Matsuda, H., Miyazawa, K. and Ito, K.: A mitogenic agglutinin from the red alga *Carpopeltis flabellata*. Phytochemistry, 26, 1335-1338 (1987)), *Hypnea japonica*-derived lectin Hypnin A-1 (see Hori, K., Miyazawa, K., Fusetani, N., Hashimoto, K. and Ito, K.: Hypnins, low-molecular weight peptidic agglutinins isolated from a marine red alga, *Hypnea japonica*. Biochim. Biophys. Acta, 873, 228-236 (1986); Hori, K., Matsubara, K. and Miyazawa, K.: Primary structures of two hemagglutinins from the marine red alga, *Hypnea japonica*. Biochim. Biophys. Acta, 28, 226-236 (2000)), BML-17, *Bryopsis plumosa*-derived lectin BPL-54, *Codium fragile*-derived lectin CFA.

Terrestrial plant-derived lectins: *Canavallia ensiformis*-derived lectin Con A (Edelman, G. M. et al., PNAS, USA, 62, 2580-2585 (1972)), *Ulex europaeus*-derived lectin UEA-I (Horejsi, V. and Kocourek, J., Biochim. Biophys. Acta, 336, 329-337 (1974)), *Arachis hypogaea*-derived lectin PNA (Lotan, R. Et al., J. Biol. Chem., 250, 8518-8523 (1975)), *Glycine max*-derived lectin SBA (Pereira, M. E. A. et al., Crabohydr. Res., 37, 89-102 (1974)), *Triticum aestivum*-derived lectin WGA (Peumans, W. J. et al., Planta, 154, 562-568 (1982)), *Maackia amurensis*-derived lectin MAH (Kawaguchi, T. et al., J. Biol. Chem., 249, 2768-2792 (1974)), *Galanthus nivalis*-derived lectin GNA (Van Damme, E. J. M. et al., FEBS lett., 215, 140-144 (1987)).

The terrestrial plant-derived lectins were purchased from COSMO BIO CO., LTD., for example.

(Method)
Assessment was made as to affinity of the different types of lectins and chicken egg yolk antibody (chicken IgY antibody). Briefly, using Biacore 2000 (BIACORE) that employs the principle of surface plasmon resonance method (hereinafter, "SPR method"), chicken egg yolk antibodies (chicken IgY antibodies) were immobilized as ligands on a sensor chip, and measurements were made according to manuals using each type of lectin solution as an analyte. The SPR technique allows for measurement of specific interactions between biomolecules both quickly and quantitatively, without labeling the biomolecules. According to this technique, the ligands are immobilized on a surface of the sensor chip, which is then supplemented with a solution of substance (analyte) that acts on the ligand. Slight changes in mass caused by the binding and dissociation of the molecules are then detected as changes in SPR signals. The mass change is represented by resonance unit (RU). One thousand RU is equivalent to a change in reflection angle of $0.1°$ caused by resonance, and it means that the analyte has bound to the ligand at 1 ng/mm$^2$. The surface of the sensor chip is coated with dextran, and the ligands are immobilized primarily via carboxyl groups that have been introduced into the dextran.

Note that, as permitted, the lectins tested as analytes were selected to have different sugar binding specificity. The chicken egg yolk antibody (chicken IgY antibodies) tested as ligands were obtained by purification from egg yolk, using Eggcellent Chicken IgY Purification Kit (Pierce Chem. Co. USA).

(Results)
The foregoing assessment revealed that the binding to chicken egg yolk antibody (chicken IgY antibodies) occurs in algae-(seaweed)-derived lectins ESA-2, Solnin B, BCL, Carnin, Hypnin A-1, BML-17, and in terrestrial plant-derived lectins Con A and UEA-I. All of these lectins had affinity to the high-mannose-type sugar chains, except for Hypnin A-1 and UEA-I.

Example 4

Assessment of Affinity Between Chicken Egg Yolk Antibody (Chicken IgY Antibody) and Lectins (Test Lectins)
Algae-(seaweed)-derived lectins: ESA-2, Solnin B, Carnin, Hypnin A-1, BML-17
Terrestrial Plant-Derived Lectin: Con A
(Method)
The following was immobilized on a CM5 sensor chip (BIACORE): Taka-amylase A having only the high-mannose-type sugar chain (purified from Taka-diastase (derived from *Aspergillus*, Sankyo) using Con A-immobilization column; asialotransferrin having only the complex-type sugar chain (obtained by purifying transferrin that had been treated with dilute fetuiacids (desialyated transferrin) (derived from human, SIGMA) using reversed phase HPLC with ODS column); bovine tyroglobulin (derived from cattle, SIGMA) having both the high-mannose-type sugar chain and the complex-type sugar chain; antibody (chicken IgY antibody); and bovine serum albumin (BSA, SIGMA) as a control. Immobilization was performed according to manuals. Specifically, Taka-amylase A was immobilized using a surface thiol coupling method, and asialofetuin, bovine tyroglobulin, antibody, and BSA were immobilized using an amine coupling method. Each sample was immobilized in an amount within a range of 1000 RU to 1500 RU as adjusted by a manual injection method. Purity of the glycoprotein was confirmed by SDS-PAGE or MALDI-TOF-MS.

Affinity between each glycoprotein and each lectin was analyzed by SPR technique. Prior to analysis, preliminary analyses were made to assess analysis methods. Kinetics analysis employing a non-linear least square method was found to be suitable. Approximate $K_D$ values were calculated from a resulting sensorgram, and five or more steps of two-fold series dilutions of analyte (lectin) were prepared at target concentrations of 0.1 to 10 $K_D$ [M]. An analysis program was created using "Customized Application" according to the manual, and a subtraction function was used in which subtraction was made from flow cells that had glycoproteins immobilized thereon, from among four flow cells in the sensor chip. As a control, one of the four flow cells that did not immobilize any substance was used (flow cell 1). Under this analysis program, each analyte (lectin) solution was flown on the sensor chip at a flow rate of 30 μl/min for 3 minutes, and buffer was flown for 3 minutes to measure the amount of lectin that had bonded/dissociated. Note that, an increase in RU during the time period from 10 seconds before addition of the analyte and to 10 seconds before the end of addition of analyte was given as the amount of bonding. A decrease in RU in the time period from 10 seconds after the addition of buffer to 10 seconds before the end of addition of buffer was given as the amount of dissociation.

Next, the sensor chip was washed with 0.5 M D-mannose, 10 mM glycine-HCl (pH 4.0), 50 mM HCl, and 10 mM NaOH for reproduction. Concerning the resulting sensorgram, the bonding phase and dissociation phase were fitted together with the curve to determine a bonding rate constant Ka, a dissociation rate constant kd, an affinity constant $K_A$, and a dissociation constant $K_D$.

(Results)

Table 1 represents affinity constants of chicken egg yolk antibody and the various lectins. Table 1 represents bonding rate constant Ka ($M^{-1}s^{-1}$), dissociation rate constant Kd ($s^{-1}$), affinity constant $K_A$ ($M^{-1}$), and dissociation constant $K_D$ (M). The greater the affinity constant, the greater the affinity (stronger binding).

As can be seen from Table 1, the tested lectins all had high affinity for chicken egg yolk antibody (affinity constant $K_A=10^7$ to $10^8$ $M^{-1}$), and bovine tyroglobulin (affinity constant $K_A=10^7$ to $10^8$ $M^{-1}$). Carnin (affinity constant $K_A=10^8$ $M^{-1}$) and Con A (affinity constant $K_A=10^6$ $M^{-1}$) had high affinity also for asialotransferrin. Further, all tested lectins except HypninA-1 had high affinity for Taka-amylase A (affinity constant $K_A=10^7$ to $10^8$ $M^{-1}$).

As shown by these results, no lectin was found that specifically bonded only to chicken egg yolk antibody. It was found, however, that the bonding between four kinds of seaweed lectins (ESA-2, Solnin B, BML-17, and Carnin) and chicken egg yolk antibody was mediated by the bond with the high-mannose-type sugar chain. Note that, BML-17, ESA-2, Hypnin A-1, Carnin, and Con A had increasing affinity to chicken egg yolk antibody in this order.

Example 5

Assessment of Elutability of Various Lectins and Bovine Tyroglogulin (Method)

As in the case of chicken egg yolk antibody, a chip having immobilized thereon bovine tyroglogulin including the high-mannose-type sugar chain and the complex-type sugar chain was used to assess elutability of lectins that had bound to the chip. Note that, tyroglogulin was immobilized in a maximum amount (12,095 RU) on CM5 sensor chip, so as to make it easier to confirm specific binding and elution. Each solution of analyte (lectin) contained in HBS-EP (equilibrated) buffer (BIACORE) at a concentration of 100 μg/ml was flown at a flow rate of 5 μl/min until the amount of bonding reached equilibrium. After washing with HBS-EP buffer and the dissociation has reached equilibrium, 50 μl of 0.5 M D-mannose in the same buffer was injected. Based on the sensorgram, the amount of binding (RU) at the time when 50 μl (5 μg) of analyte (lectin) solution was injected was measured. Then, the amount of residual bonding (RU) of analyte (lectin) after buffer washing and elution with 50 μl of 0.5 M D-mannose was measured. The amount of residual bonding was given by percentage with respect to the maximum amount of bonding.

(Results)

FIG. 9 shows a sensorgram representing interactions between immobilized tyroglobulin and various lectins. FIG. 3 represents the amount of residual bonding (%) of analyte (lectin) after the bonding, washing, and elution with 0.5 M D-mannose. FIG. 3 represents relative amounts of lectin that remain bonded to the chip after the dissociation with HBS-EP buffer, and relative amounts of lectin that remain after the elution with 0.5M D-mannose, when the amount of lectin binding to the bovine tyroglobulin immobilized chip exposed to the respective lectins is taken at 100%.

It was found from these results that BML-17 and Carnin were specifically and quantitatively eluted with D-mannose. ESA-2, Solnin B, and Hypnin A-1 were not eluted with D-mannose or any other eluents (results not shown). Con A was partially eluted with D-mannose.

The foregoing results revealed that BML-17 and Carnin were indeed applicable as ligands for the purification of chicken antibody.

Example 6

Purification of Chicken Egg Yolk Antibody Using BML-17 Column, Carnin Column, and Con A Column (Methods)

BML-17, Carnin, and Con A were each immobilized on HiTrap NHS-activated HP Column (1 ml volume gel, (Amersham Bioscience Corp)). Immobilization was performed according to the manual attached to the HiTrap column. For BML-17 and Con A, the inhibitory monosaccharides D-mannose and methyl-α-D-mannoside were respectively added to the ligand solutions to a final concentration of 0.2 M, so as to block the active sites of these lectins immobilized on the column. The amount of lectin immobilized on each column after thorough washing with equilibriated buffer (0.05 M tris-hydrochloric acid buffer (pH 7.5) containing 0.15 M NaCl and 0.02% $NaN_3$) was 400 μg for BML-17, 570 μg for Carnin, and 270 μg for Con A. As a control for comparison, HiTrap IgY Purification HP Column (Amersham Bioscience Corp, 5 ml volume gel, hereinafter "IgY purifying column") was used.

The columns immobilizing the respective lectins will be referred to as "BML-17 column," "Carnin column," and "Con A column," respectively.

(Results)

Figures 4A, 4B, 4C, 4D:
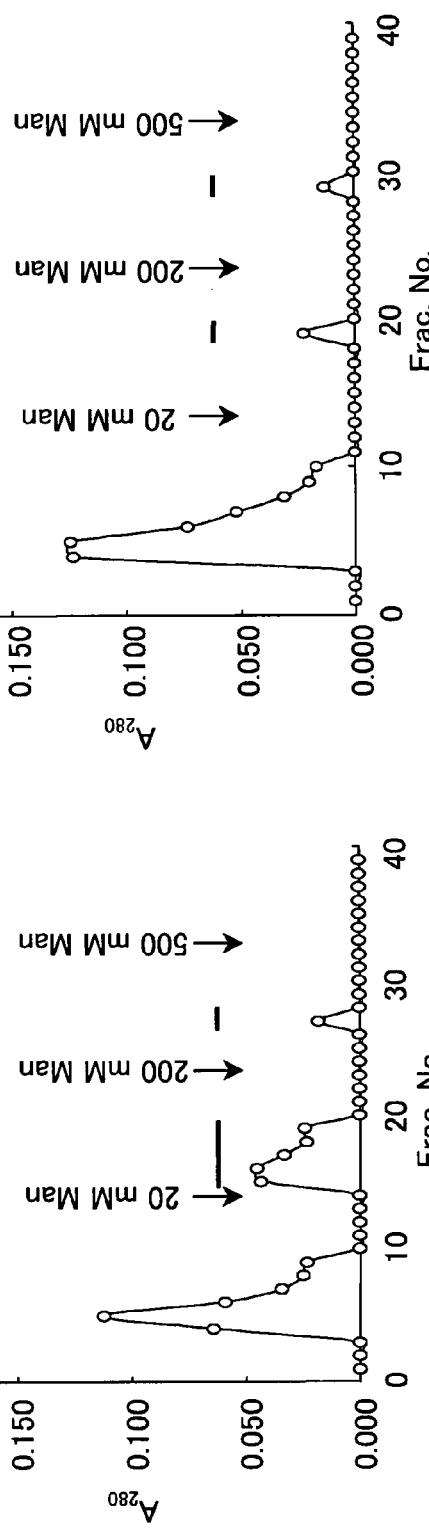
FIG. 4(a) is a diagram representing a result of monitoring protein behaviors at UV 280 nm absorption ($A_{280}$), when chicken egg yolk antibody was passed through the column (BML-17 column) immobilizing the lectin, and when elution was performed with D-mannose, in an experiment performed in Example 6.
FIG. 4(b) is a diagram representing a result of monitoring protein behaviors at UV 280 nm absorption ($A_{280}$), when chicken egg yolk antibody was passed through the column (Carnin column) immobilizing the lectin, and when elution was performed with D-mannose, in an experiment performed in Example 6.
FIG. 4(c) is a diagram representing a result of monitoring protein behaviors at UV 280 nm absorption ($A_{280}$), when chicken egg yolk antibody was passed through the column (Con A column) immobilizing the lectin, and when elution was performed with D-mannose, in an experiment performed in Example 6.
FIG. 4(d) is a diagram representing a result of monitoring protein behaviors at UV 280 nm absorption ($A_{280}$), when chicken egg yolk antibody was passed through the IgY purifying column (commercial product), and when elution was performed with elution buffer (commercial product), in an experiment performed in Example 6.

FIG. 4 represents results of monitoring protein behaviors at UV 280 nm absorption (denoted by "$A_{280}$" in FIG. 4 and elsewhere), when chicken egg yolk antibody was passed through the columns immobilizing the respective lectins ("BML-17 column," "Carnin column," and "Con A column") and the IgY purifying column, and when elution was performed with D-mannose or elution buffer. FIG. 4(a) shows the result for BML-17 column. FIG. 4(b) shows the result for Carnin column. FIG. 4(c) shows the result for Con A column. FIG. 4(d) shows the result for IgY purifying column.

As a result of supplying the chicken egg yolk antibody to the four kinds of columns, the antibody bound to all of these columns. The results of elution with 20 mM, 200 mM, and 500 mM D-mannose revealed that specific elution of chicken egg yolk antibody with D-mannose was possible with BML- 17 column and Carnin column (FIGS. 4(a) and 4(b)). As will be described later with reference to FIG. 5, BML-17 column was most effective in terms of the recovery rate of chicken egg yolk antibody.

In Con A column, elution occurred with 200 mM methyl-α-D-mannoside (FIG. 4(c)); however, the efficiency of purification was considerably low in the commercially available IgY column whose affinity principle is based on affinity of thiol (FIG. 4(d), FIG. 5).

Example 7

Purification of Chicken Monoclonal Antibody from Hybridoma Culture Supernatent Using BML-17 Column, Carnin Column, and Con A Column (Method)

Purification of chicken monoclonal antibody from hybridoma culture supernatant was intended using BML-17 column, Carnin column, Con A column, IgY purifying column, and Con A Sepharose 4B Lab Packs column (Amersham Bioscience Corp, hereinafter "commercially available Con A column") (5 ml volume gel, 10 to 16 mg/ml of immobilized Con A).

Specifically, 5 ml of hybridoma culture supernatant (2.5 ml in the case of commercially available Con A column) was directly added to each column. After thoroughly washing the column with 1M NaCl, elution was performed with 500 mM D-mannose or 500 mM methyl-α-D-mannoside for the columns immobilizing the lectins, and with elution buffer for the IgY purifying column as specified by the manual. Each eluate was subjected to SDS-PAGE (4 to 20% gradient gel (e-PA-GEL, ATTO)). Bands were detected by CBB staining and western blotting. For quantification of active chicken monoclonal antibody in the eluate, a sandwich ELISA method was used. Western blotting used horseradish peroxidase (HRP)-labeled goat anti-chicken IgG antibody (COSMO BIO CO., LTD.). Konica immunostain-HRP (Seikagaku Corporation) was used for staining.

For hybridoma, anti-DNP-antibody-producing B4 cells were used that were obtained by fusing MUH1 derived from chicken B cells with DNP-KLH immunized chicken splenocytes. The B4 cells were cultured for 4 to 5 days in 10% FBS-Iscove's medium at 38.5° C. in $CO_2$. The culture solution was centrifuged and supernatant was supplied to the test. The hybridoma was produced by the inventors of the present invention.

The sandwich ELISA method was performed using a micro plate. Fifty μl of DNP-BSA solution (10 μg/ml) was added to each well of the plate, and was allowed to stand for 16 hours at 4° C. to solidify the antigen. Each well was blocked with PBS containing 0.2% skimmed milk. After washing with PBS containing 0.5% Tween20, 50 μl of test solution adjusted with PBS containing 0.1% skimmed milk was added to each well and was allowed to stand for 1 hour at 37° C. After washing the plate, 50 μl of HRP-labeled goat anti-chicken IgG antibody solution (1 μg/ml) was added to each well, and was allowed to stand for 1 hour at 37° C. After thoroughly washing the plate, 100 μl of coloring reagent (Konica immunostain) was added to each well, and was allowed to stand for 10 minutes at room temperature. Absorbance at 415 nm in each well was measured with a microplate reader (BIO-RAD Model 550). Note that, a standard analytical curve was drawn by performing a similar measurement for the chicken anti-DNP-KLH monoclonal antibody sample.

(Results)

FIG. 5 represents results of monitoring protein behaviors at UV 280 nm absorption (denoted by "$A_{280}$" in FIG. 5 and elsewhere), when the hybridoma culture supernatant was passed through the columns immobilizing the respective lectins ("BML-17 column," "Carnin column," "Con A column," and "Con A-HiTrap column") and the IgY purifying column, and when elution was performed with 500 mM D-mannose or elution buffer. FIG. 5(a) shows the result for BML-17 column. FIG. 5(b) shows the result for Carnin column. FIG. 5(c) shows the result for Con A column. FIG. 5(d) shows the result for the commercially available Con A column. FIG. 5(e) shows the result for IgY purifying column.

FIG. 6 shows the results of analysis of the eluates by western blotting (FIG. 6(a)) and SDS-PAGE (FIG. 6(b)). Lanes 1 and 11 represent molecular weight markers. Lanes 2 and 10 represent chicken monoclonal antibody sample. Lane 3 represents 10% FBS-Iscove's medium. Lane 4 represents hybridoma culture supernatant. Lane 5 represents an elution fraction for BML-17 column. Lane 6 represents an elution fraction for Carnin column. Lane 7 represents an elution fraction for Con A column. Lane 8 represents an elution fraction for IgY purifying column. Lane 9 represents an elution fraction for commercially available Con A column.

It was found from FIGS. 5 and 6 that the use of BML-17 column and Carnin column allows for purification of very pure chicken monoclonal antibody in one step from the hybridoma culture supernatant. On the other hand, purified samples from the commercially available Con A-HiTrap column or IgY purifying column contained a large quantity of foreign substances.

Table 6 represents purification efficiency of active chicken monoclonal antibody from the hybridoma culture supernatant supplied to the respective columns.

As can be seen from Table 6, the yield of active chicken monoclonal antibody per amount of immobilized ligand was the highest in BML-17, followed by Carnin column.

As shown by the foregoing results, the use of BML-17 column and Carnin column allows for very simple purification without combining multi-stages of classic protein purification methods to purify chicken monoclonal antibody from the hybridoma culture supernatant as conventionally done.

The present invention is not limited to the description of the embodiments above, but may be altered by a skilled person within the scope of the claims. An embodiment based on a proper combination of technical means suitably modified within the scope of claims is encompassed in the technical scope of the present invention.

[Tables for Examples]

TABLE 1

| Lectin | Binding Rate Constant ka[$M^{-1}s^{-1}$] | Dissociation Rate Constant kd[$s^{-1}$] | Affinity Constant $K_A$[$M^{-1}$] | Dissociation Constant $K_D$[M] |
|---|---|---|---|---|
| ESA-2 | $3.52 \times 10^5$ | $4.55 \times 10^{-3}$ | $7.73 \times 10^7$ | $1.29 \times 10^{-8}$ |
| Solnin B | $1.62 \times 10^5$ | $5.64 \times 10^{-3}$ | $2.88 \times 10^7$ | $3.47 \times 10^{-8}$ |
| BML-17 | $4.90 \times 10^5$ | $5.86 \times 10^{-3}$ | $8.36 \times 10^7$ | $1.20 \times 10^{-8}$ |
| Carnin | $1.13 \times 10^5$ | $1.72 \times 10^{-3}$ | $6.57 \times 10^7$ | $1.52 \times 10^{-8}$ |
| Hypnin A-1 | $2.12 \times 10^4$ | $2.98 \times 10^{-4}$ | $7.10 \times 10^7$ | $1.41 \times 10^{-8}$ |
| Con A | $4.67 \times 10^2$ | $2.49 \times 10^{-5}$ | $1.87 \times 10^7$ | $5.34 \times 10^{-8}$ |

TABLE 2

| Carbohydrate and glycoprotein | Minimum inhibitory concentration (mM or μg/ml) |
|---|---|
| Monosaccharide (mM) | |
| D-Glucose | — |
| D-Galactose | — |
| D-Mannose | 12.5 |
| N-Acetyl-D-glucosamine | — |
| N-Acetyl-D-galactosamine | — |
| Fructose | — |
| D-Xylose | — |
| L-Fucose | — |
| Oligosaccharide (mM) | |
| Lactose | — |
| Raffinose | — |
| Glycoprotein (μg/ml) | |
| Transferrin | 2000 |
| Asialotransferrin | 1000 |
| Fetuin | 1000 |
| Asialofetuin | 500 |
| α1-Acid glycoprotein | — |
| Asialo-α1-acid glycoprotein | NT |
| Yeast mannan | 7.8 |
| Mucin | 250 |
| Asialomucin | 250 |

—; No inhibition at 100 mM of mono- or oligosaccharides, or at 2 mg/ml of glycoproteins

TABLE 3

R, GN β 1-4GN-PA; R*, GN β 1-4(Fuc α 1-6)GN-PA; GA, Galactose; GAN, N-acetyl galactosamine; G, Glucose; GN, N-acetyl glucosamine; M, Mannose; PA, Pyridylaminated.

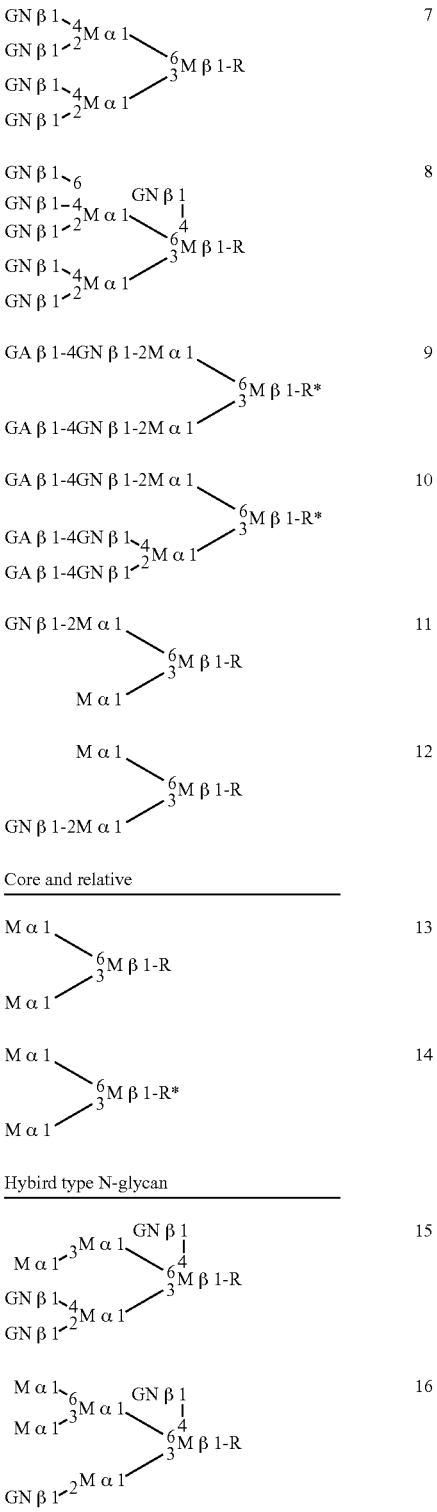

TABLE 3-continued

R, GN β 1-4GN-PA; R*, GN β 1-4(Fuc α 1-6)GN-PA;
GA, Galactose; GAN, N-acetyl galactosamine; G,
Glucose; GN, N-acetyl glucosamine; M, Mannose;
PA, Pyridylaminated.

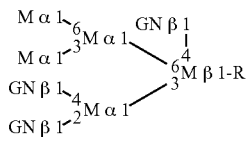  17

TABLE 4

R, GN β 1-4GN-PA; R*, GN β 1-4(Fuc α 1-6)GN-PA;
GA, Galactose; GAN, N-acetyl galactosamine; G,
Glucose; GN, N-acetyl glucosamine; M, Mannose;
PA, Pyridylaminated.

High mannose type N-glycan

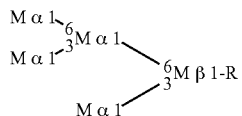  18

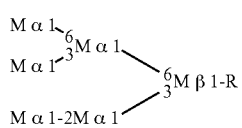  19

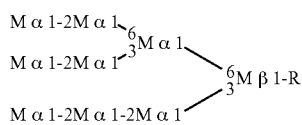  20

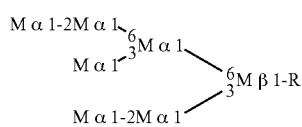  21

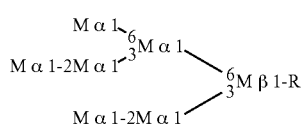  22

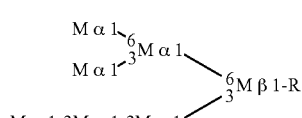  23

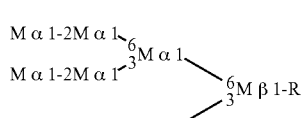  24

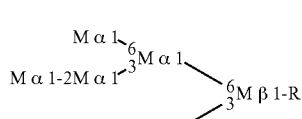  25

TABLE 4-continued

R, GN β 1-4GN-PA; R*, GN β 1-4(Fuc α 1-6)GN-PA;
GA, Galactose; GAN, N-acetyl galactosamine; G,
Glucose; GN, N-acetyl glucosamine; M, Mannose;
PA, Pyridylaminated.

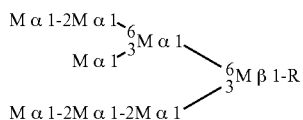  26

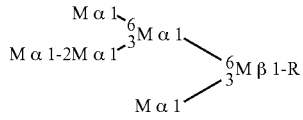  27

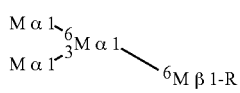  28

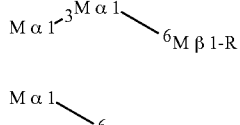  29

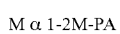  30

Oligomannose

M α 1-2M-PA  31
M α 1-3M-PA  32
M α 1-6M-PA  33

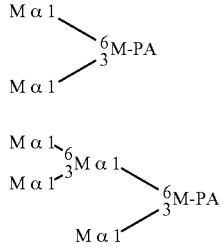  34

  35

M-PA  36

Sugar chain of glycolipid

GA β 1-3GAN β 1-4GA β 1-4G-PA  37
GAN β 1-4GA β 1-4G-PA  38
GA α 1-4GA β 1-4G-PA  39
GAN β 1-3GA α 1-4GA β 1-4G-PA  40
GAN α 1-3GAN β 1-3GA α 1-4GA β 1-4G-PA  41
GA β 1-3GN β 1-3GA β 1-4G-PA  42

  43

  44

TABLE 5

| Oligosaccharide | Binding activity (%) |
|---|---|
| Complex type | |
| 1 | 13.5 |
| 2 | 7.0 |
| 3 | 1.5 |
| 4 | 1.0 |
| 5 | 10.2 |
| 6 | 10.6 |
| 7 | 0.9 |
| 8 | 0 |
| 9 | 9.0 |
| 10 | 13.6 |
| 11 | 8.3 |
| 12 | 7.0 |
| Core and relative | |
| 13 | 19.8 |
| 14 | 15.8 |
| Hybrid type | |
| 15 | 0 |
| 16 | 8.8 |
| 17 | 0 |
| High mannose type | |
| 18 | 32.7 |
| 19 | 39.4 |
| 20 | 70.1 |
| 21 | 41.0 |
| 22 | 32.6 |
| 23 | 49.4 |
| 24 | 47.5 |
| 25 | 28.1 |
| 26 | 53.0 |
| 27 | 54.1 |
| 28 | 19.1 |
| 29 | 0 |
| 30 | 0 |
| Oligomannose | |
| 31 | 0 |
| 32 | 0 |
| 33 | 0 |
| 34 | 0 |
| 35 | 14.2 |
| 36 | 0 |

TABLE 5-continued

| Oligosaccharide | Binding activity (%) |
|---|---|
| Oligosaccharide of glycolipid | |
| 37 | 14.2 |
| 38 | 12.7 |
| 39 | 0 |
| 40 | 0 |
| 41 | 0 |
| 42 | 0 |
| 43 | 0 |
| 44 | 7.2 | a; Not tested

TABLE 6

| Affinity Column | Column Volume (ml) | Amount of Ligand (mg) | Added Sample | Amount of Active Chicken Monoclonal Antibody (μg) Eluted (Purified) Fraction |
|---|---|---|---|---|
| BML-17-Immobilized Column | 1 | 0.40 | 9.63 | 2.17 |
| Carnin-Immobilized Column | 1 | 0.57 | 9.63 | 1.85 |
| IgY-Purifying Column | 5 | 15 | 9.63 | 0.67 |
| Commercial Con A Column | 5 | 50-80 | 4.82 | 2.06 |

INDUSTRIAL APPLICABILITY

As described above, a peptide of the present invention is applicable for the purification of chicken antibodies (polyclonal antibodies, monoclonal antibodies, etc.) in particular. Since antibodies, including the chicken antibody, are useful in medical applications, the present invention is applicable to a wide range of industry, including medical industry, pharmaceutical industry, and industries relating to test agents.

---

The invention claimed is:

1. An isolated polypeptide consisting of the amino acid sequence of SEQ ID NO:2.

2. An isolated polynucleotide encoding a polypeptide, wherein the polypeptide consists of the amino acid sequence of SEQ ID NO:2.

3. The isolated polynucleotide as set forth in claim 2, wherein the isolated polynucleotide consists of the nucleotide sequence of SEQ ID NO:1.

4. A vector comprising the isolated polynucleotide of claim 2.

5. A method for producing a polypeptide consisting of the amino acid sequence of SEQ ID NO:2, the method comprising the steps of:

culturing an isolated host cell comprising the vector of claim 4, and producing the polypeptide consisting of the amino acid sequence of SEQ ID NO:2.

6. An isolated host cell comprising the vector of claim 4.

7. A detecting instrument comprising the isolated polynucleotide of claim 4 immobilized on a substrate.

8. A detecting instrument comprising the isolated polypeptide of claim 1 immobilized on a substrate.

9. A support comprising the isolated polypeptide of claim 1 immobilized thereto.

* * * * *

SEQUENCE LISTING

<160> NUMBER OF SEQ ID NOS: 17

<210> SEQ ID NO 1
<211> LENGTH: 504
<212> TYPE: DNA
<213> ORGANISM: Bryopsis maxima

<400> SEQUENCE: 1

```
gtcatatacc aagaccccgt aacttcagat atgttcgcga agattccgat gccggggcac      60
cgtggaccgt ggtacgtctg ccactcgtcg ggtgactggt cgagaaacga gcctgttttc     120
ggccgttgtg ccctggatgc taagggcatg gtcgaggcgt acttccccta tggaggtaaa     180
gacatcaagt ggccttcacg ctggtccgca gtcttgacca ccggtgtgta ttggggaaag     240
tacaacgact ggaaacaagc ggattgcaat gggggtcaac aagtggtgga cggcggtaga     300
ggggccgtga cagtcaggat ggacggactc tcggagtgca agggctggac aacgggtaag     360
agcagtcata acgaggtctg gttcggatgt aacggaaagg aggtgggtag ctggctgtct     420
```

```
gatacccctg ccagcgacgt tttccctctg tgccaggagt atggagcggc agtaaaattg    480
gtccacatgg ggcgcgcttt caac                                           504
```

<210> SEQ ID NO 2
<211> LENGTH: 168
<212> TYPE: PRT
<213> ORGANISM: Bryopsis maxima

<400> SEQUENCE: 2

```
Val Ile Tyr Gln Asp Pro Val Thr Ser Asp Met Phe Ala Lys Ile Pro
 1               5                  10                  15

Met Pro Gly His Arg Gly Pro Trp Tyr Val Cys His Ser Ser Gly Asp
            20                  25                  30

Trp Ser Arg Asn Glu Pro Val Phe Gly Arg Cys Ala Leu Asp Ala Lys
        35                  40                  45

Gly Met Val Glu Ala Tyr Phe Pro Tyr Gly Lys Asp Ile Lys Trp
    50                  55                  60

Pro Ser Arg Trp Ser Ala Val Leu Thr Thr Gly Val Tyr Trp Gly Lys
65                  70                  75                  80

Tyr Asn Asp Trp Lys Gln Ala Asp Cys Asn Gly Gly Gln Gln Val Val
                85                  90                  95

Asp Gly Gly Arg Gly Ala Val Thr Val Arg Met Asp Gly Leu Ser Glu
            100                 105                 110

Cys Lys Gly Trp Thr Thr Gly Lys Ser Ser His Asn Glu Val Trp Phe
        115                 120                 125

Gly Cys Asn Gly Lys Glu Val Gly Ser Trp Leu Ser Asp Thr Pro Ala
    130                 135                 140

Ser Asp Val Phe Pro Leu Cys Gln Glu Tyr Gly Ala Ala Val Lys Leu
145                 150                 155                 160

Val His Met Gly Arg Ala Phe Asn
                165
```

<210> SEQ ID NO 3
<211> LENGTH: 11
<212> TYPE: PRT
<213> ORGANISM: Bryopsis maxima

<400> SEQUENCE: 3

```
Asp Met Phe Ala Lys Ile Pro Met Pro Gly His
 1               5                  10
```

<210> SEQ ID NO 4
<211> LENGTH: 8
<212> TYPE: PRT
<213> ORGANISM: Bryopsis maxima

<400> SEQUENCE: 4

```
Ala Lys Gly Met Val Glu Ala Tyr
 1               5
```

<210> SEQ ID NO 5
<211> LENGTH: 11
<212> TYPE: PRT
<213> ORGANISM: Bryopsis maxima

<400> SEQUENCE: 5

```
Tyr Gln Asp Pro Val Thr Ser Asp Met Phe Glu
 1               5                  10
```

```
<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Primer Sequence
<220> FEATURE:
<221> NAME/KEY: unsure
<222> LOCATION: (12)..(12)
<223> OTHER INFORMATION: n stands for any base
<220> FEATURE:
<221> NAME/KEY: unsure
<222> LOCATION: (21)..(21)
<223> OTHER INFORMATION: n stands for any base
<220> FEATURE:
<221> NAME/KEY: unsure
<222> LOCATION: (27)..(27)
<223> OTHER INFORMATION: n stands for any base
<220> FEATURE:
<221> NAME/KEY: unsure
<222> LOCATION: (30)..(30)
<223> OTHER INFORMATION: n stands for any base

<400> SEQUENCE: 6
gacatgttcg cnaagatycc natgccnggn ca                                 32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
gtacgcctcg accaccacgc ccttagcatc ca                                 32

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
ccaagacccc gtaacttcag atatgttcg                                     29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
aaccctcact aaagggaaca aaagctgga                                     29

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
```
ttgtaatacg actcactata gggcga                                                26

<210> SEQ ID NO 11
<211> LENGTH: 576
<212> TYPE: DNA
<213> ORGANISM: Bryopsis maxima

<400> SEQUENCE: 11
gccgcacttg gtgatgcacg gccagttgtc aaccagatgg ccaacgtcac gacgatgatg      60
gttgaaaacg tcatatacca agaccccgta acttcagata tgttcgcgaa gattccgatg     120
ccggggcacc gtgaccgtg gtacgtctgc cactcgtcgg gtgactggtc gagaaacgag     180
cctgttttcg gccgttgtgc cctggatgct aagggcatgg tcgaggcgta cttcccctat     240
ggaggtaaag acatcaagtg gccttcacgc tggtccgcag tcttgaccac cggtgtgtat     300
tggggaaagt acaacgactg gaaacaagcg gattgcaatg ggggtcaaca agtggtggac     360
ggcggtagag gggccgtgac agtcaggatg gacggactct cggagtgcaa gggctggaca     420
acgggtaaga gcagtcataa cgaggtctgg ttcgatgta acggaaagga ggtgggtagc      480
tggctgtctg ataccctgc cagcgacgtt tccctctgt gccaggagta tggagcggca      540
gtaaaattgg tccacatggg gcgcgctttc aactaa                               576

<210> SEQ ID NO 12
<211> LENGTH: 191
<212> TYPE: PRT
<213> ORGANISM: Bryopsis maxima

<400> SEQUENCE: 12

Ala Ala Leu Gly Asp Ala Arg Pro Val Val Asn Gln Met Ala Asn Val
 1               5                  10                  15

Thr Thr Met Met Val Glu Asn Val Ile Tyr Gln Asp Pro Val Thr Ser
                20                  25                  30

Asp Met Phe Ala Lys Ile Pro Met Pro Gly His Arg Gly Pro Trp Tyr
            35                  40                  45

Val Cys His Ser Ser Gly Asp Trp Ser Arg Asn Glu Pro Val Phe Gly
        50                  55                  60

Arg Cys Ala Leu Asp Ala Lys Gly Met Val Glu Ala Tyr Phe Pro Tyr
 65                  70                  75                  80

Gly Gly Lys Asp Ile Lys Trp Pro Ser Arg Trp Ser Ala Val Leu Thr
                85                  90                  95

Thr Gly Val Tyr Trp Gly Lys Tyr Asn Asp Trp Lys Gln Ala Asp Cys
                100                 105                 110

Asn Gly Gly Gln Gln Val Val Asp Gly Gly Arg Gly Ala Val Thr Val
            115                 120                 125

Arg Met Asp Gly Leu Ser Glu Cys Lys Gly Trp Thr Thr Gly Lys Ser
        130                 135                 140

Ser His Asn Glu Val Trp Phe Gly Cys Asn Gly Lys Glu Val Gly Ser
145                 150                 155                 160

Trp Leu Ser Asp Thr Pro Ala Ser Asp Val Phe Pro Leu Cys Gln Glu
                165                 170                 175

Tyr Gly Ala Ala Val Lys Leu Val His Met Gly Arg Ala Phe Asn
            180                 185                 190

<210> SEQ ID NO 13
<211> LENGTH: 28
<212> TYPE: PRT
<213> ORGANISM: Bryopsis maxima

<400> SEQUENCE: 13

Val Ile Tyr Gln Asp Pro Val Thr Ser Asp Met Phe Ala Lys Ile Pro
1               5                   10                  15

Met Pro Gly His Arg Gly Pro Trp Tyr Val Met His
            20                  25

<210> SEQ ID NO 14
<211> LENGTH: 10
<212> TYPE: PRT
<213> ORGANISM: Bryopsis corticulans

<400> SEQUENCE: 14

Ser Asp Leu Pro Thr Gly Asp Phe Phe Leu
1               5                   10

<210> SEQ ID NO 15
<211> LENGTH: 23
<212> TYPE: PRT
<213> ORGANISM: Bryopsis plumosa
<220> FEATURE:
<221> NAME/KEY: UNSURE
<222> LOCATION: (6)..(6)
<223> OTHER INFORMATION: Unknown

<400> SEQUENCE: 15

Ser Asp Leu Pro Thr Xaa Asp Phe Phe His Ile Pro Glu Gly Tyr Leu
1               5                   10                  15

Glu Ala Ser Asn Gly Gly Ala
            20

<210> SEQ ID NO 16
<211> LENGTH: 31
<212> TYPE: PRT
<213> ORGANISM: Bryopsis.sp
<220> FEATURE:
<221> NAME/KEY: UNSURE
<222> LOCATION: (2)..(2)
<223> OTHER INFORMATION: Unknown
<220> FEATURE:
<221> NAME/KEY: UNSURE
<222> LOCATION: (29)..(29)
<223> OTHER INFORMATION: Unknown

<400> SEQUENCE: 16

Pro Xaa Thr Ile Thr Val Phe Asn Ser Gly Gly Tyr Val Ile Lys Ser
1               5                   10                  15

Thr Phe Glu Tyr Phe Asp Asp Ala Thr Tyr Asp Ile Xaa Arg Arg
            20                  25                  30

<210> SEQ ID NO 17
<211> LENGTH: 18
<212> TYPE: PRT
<213> ORGANISM: Bryopsis.sp
<220> FEATURE:
<221> NAME/KEY: UNSURE
<222> LOCATION: (2)..(2)
<223> OTHER INFORMATION: Unknown
<220> FEATURE:
<221> NAME/KEY: UNSURE
<222> LOCATION: (17)..(17)
<223> OTHER INFORMATION: Unknown

```
<400> SEQUENCE: 17

Asp Xaa Val Trp Thr Val Glu Val Lys Gly Leu Gly Asp Arg Ser Ser
 1               5                  10                  15

Xaa Pro
```